(12) United States Patent
Celis

(10) Patent No.: US 7,422,751 B2
(45) Date of Patent: Sep. 9, 2008

(54) EPSTEIN-BARR-VIRUS-SPECIFIC IMMUNIZATION

(75) Inventor: Esteban Celis, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 282 days.

(21) Appl. No.: 10/517,800

(22) PCT Filed: Jun. 13, 2003

(86) PCT No.: PCT/US03/18682

§ 371 (c)(1),
(2), (4) Date: Sep. 12, 2005

(87) PCT Pub. No.: WO03/105665

PCT Pub. Date: Dec. 24, 2003

(65) Prior Publication Data

US 2006/0257356 A1    Nov. 16, 2006

Related U.S. Application Data

(60) Provisional application No. 60/388,625, filed on Jun. 14, 2002.

(51) Int. Cl.
*A61K 39/00* (2006.01)
*A61K 39/12* (2006.01)
*A61K 39/25* (2006.01)

(52) U.S. Cl. .............. 424/230.1; 424/185.1; 424/186.1; 424/204.1; 424/229.1

(58) Field of Classification Search ........................ None
See application file for complete search history.

(56) References Cited

U.S. PATENT DOCUMENTS

| | | | |
|---|---|---|---|
| 5,662,907 A | 9/1997 | Kubo et al. | |
| 5,869,453 A | 2/1999 | Moss et al. | |
| 6,162,440 A | 12/2000 | Hayward et al. | |

FOREIGN PATENT DOCUMENTS

| | | | |
|---|---|---|---|
| AU | WO 95/24925 | * | 9/1995 |
| WO | WO95/24925 | | 9/1995 |
| WO | WO 01/12215 | * | 2/2001 |

OTHER PUBLICATIONS

Babcock et al., "EBV Persistence in Memory B Cells In Vivo", Immunity, 1998, 9:395-404.
Cristiano et al., "Molecular conjugates: a targeted gene delivery vector for molecular medicine", J. Mol. Med., 1995, 73:479-486.
Di Tommaso et al., "Induction of Antigen-Specific Antibodies in Vaginal Secretions by Using a Nontoxic Mutant of Heat-Labile Enterotoxin as a Mucosal Adjuvant", Infect. Immunity, 1996, 64:974-979.

Finberg, "Epstein-Barr virus-specific T cells for the management of Epstein-Barr virus lymphomas", Current Opinion Oncology, 2001, 13:349-353.
Hopwood et al., "The role of EBV in post-transplant malignancies: a review", J. Clin. Pathol., 2000, 53:248-254.
Hsieh et al., "The biology of Epstein-Barr virus in post-transplant lymphoproliferative disease", Transpl. Infect. Dis., 1999, 1:204-212.
Khanna et al., "Activation and adoptive transfer of Epstein-Barr virus-specific cytotoxic T cells in solid organ transplant patients with posttransplant lymphoproliferative disease", Proc. Natl. Acad. Sci. USA, 1999, 96(18):10391-10396.
Khanna et al., "Targeting Epstein-Barr virus nuclear antigen 1 (EBNA1) through the class II pathway restores immune recognition by EBNA1-specific cytotoxic T lymphocytes: evidence for HLA-DM-independent processing", Int. Immunol., 1997, 9(10):1537-1543.
Khanna et al., "Class I Processing-Defective Burkitt's Lymphoma Cells Are Recognized Efficiently by CD4$^+$ EEBV-Specific CTLs", J. Immunol., 1997, 158(8):3619-3625.
Kieff, "Epstein-Barr Virus and Its Replication" Fields Virology, 1996, Fields, Knipe, and Howley, eds. Lipinocott-Raven Publishers, New York, pp.2343-2396.
Kobayashi et al., "Tumor-reactive T Helper Lymphocytes Recognize a Promiscuous MAGE-A3 Epitope Presented by Various Major Histocompatibility Complex Class II Alleles", Cancer Res., 2001, 61:4773-4778.
Kobayashi et al., "Defining Promiscuous MHC Class II Helper T-Cell Epitopes for the HER2/neu Tumor Antigen", Cancer Res., 2000, 60:5228-5236.
Lu et al., "Use of Two Predictive Algorithms of the World Wide Web for the Identification of Tumor-reactive T-Cell Epitopes", Cancer Res., 2000, 60:5223-5227.
Marsh, "Nomenclature for Factors of the HLA System, Update Mar. 2002", Human Immunol., 2002, 63:515-516.
Nalesnik, "Clinical and pathological features of post-transplant lymphoproliferative disorders (PTLD)", Springer Semin. Immunopathol., 1998, 20:325-342.
Nikiforow et al., "CD4$^+$ T-Cell Effectors Inhibit Epstein-Barr Virus-Induced B-Cell Proliferation", J. Virol., 2001, 75(8):3740-3752.
Paya et al., "Epstein-Barr Virus-Induced Posttransplant Lymphoproliferative Disorders", Transplantation, 1999, 68(10):1517-1525.
Penix et al., "Two Essential Regulatory Elements in the Human Interferon γ Promoter Confer Activation Specific Expression in T Cells", J. Experim. Med., 1993, 178:1483-1496.

(Continued)

*Primary Examiner*—Bruce Campell
*Assistant Examiner*—Sharon Hurt
(74) *Attorney, Agent, or Firm*—Fish & Richardson P.C.

(57) ABSTRACT

The invention provides materials and methods for using EBV EBNA2 peptide epitopes to treat and/or prevent post-transplant lymphoproliferative disorders (PTLD). The invention also provides compositions and articles of manufacture containing EBNA2 peptide epitopes that can be used to treat and/or prevent PTLD.

8 Claims, 13 Drawing Sheets

OTHER PUBLICATIONS

Rickinson et al., "Human Cytotoxic T Lymphocyte Responses to Epstein-Barr Virus Infection", Ann. Rev. Immunol., 1997, 15405-31.

Rowe, "Epstein-Barr Virus Immortalization and Latency", Front. Biosci., 1999, 4:D346-371.

Sigal et al., "Cyclosporin A, FK-506, and Rapamycin: Pharmacologic Probes of Lymphocyte Signal Transduction", Annu. Rev. Immunol., 1992, 10:510-560.

Southwood et al., "Several Common HLA-DR Types Share Largely Overlapping Peptide Binding Repertoires", J. Immunol., 1998, 160:3363-3373.

Thomson et al., "Targeting a Polyepitope Protein Incorporating Multiple Class II-Restricted Viral Epitopes to the Secretory/Endocytic Pathway Facilitates Immune Recognition by CD4[+] Cytotoxic T Lymphocytes: a Novel Approach to Vaccine Design", J. Virol., 1998, 72(3):2246-2252.

Thompson et al., "cis-Acting Sequences Required for Inducible Interleukin-2 Enhancer Function Bind a Novel Ets-Related Protein, Elf-1", Mol. And Cell. Biol., 1992, 12(3):1043-1053.

Todd et al., "Transcription of the Interleukin 4 Gene Is Regulated by Multiple Promoter Elements", J. Exp. Med., 1993, 177:1663-1674.

Yamamoto et al., "Mutants in the ADP-ribosylatransferase Cleft of Cholera Toxin Lack Diarrheagenicity by Retain Adjuvanticity", J. Exp. Med., 1997, 185(7):1203-1210.

* cited by examiner

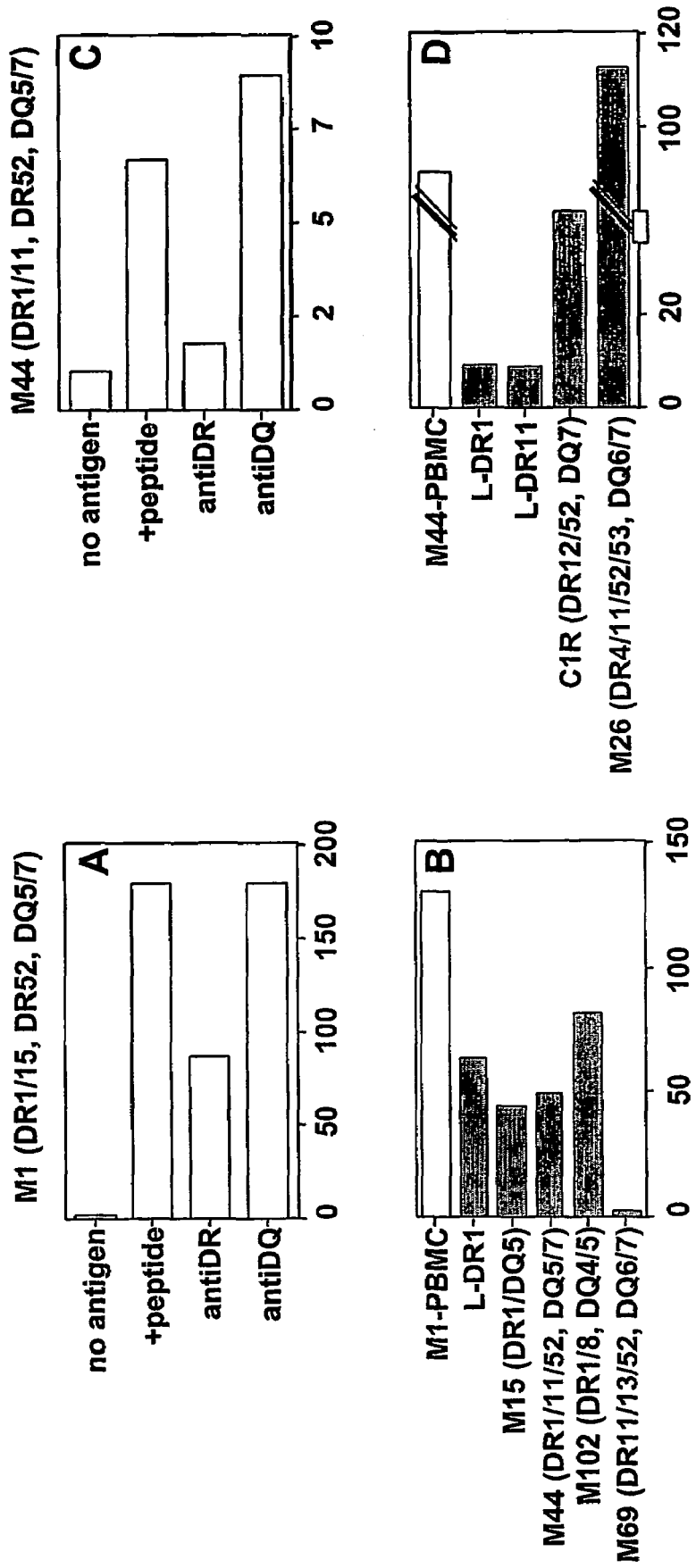
Figure 2 – page 1

Figure 2 – page 2
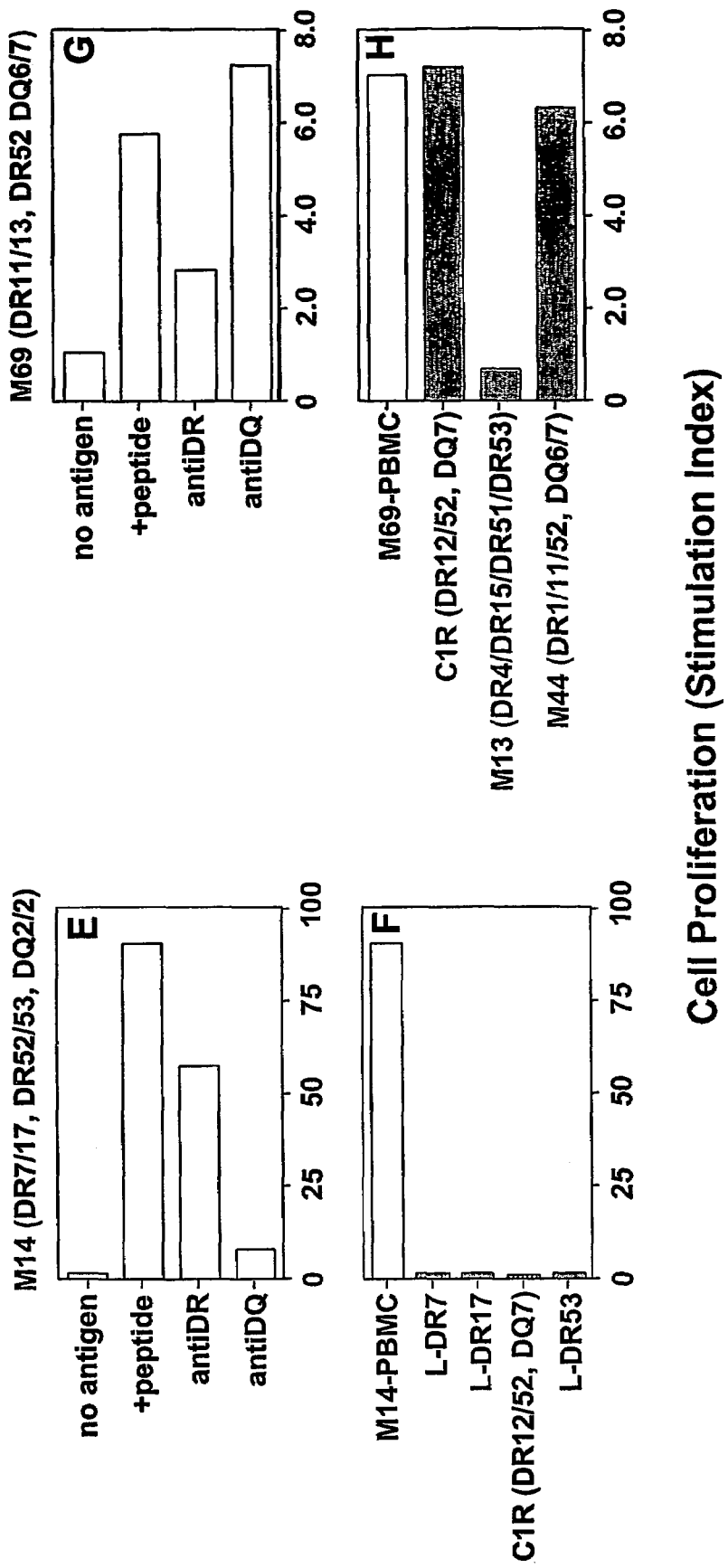

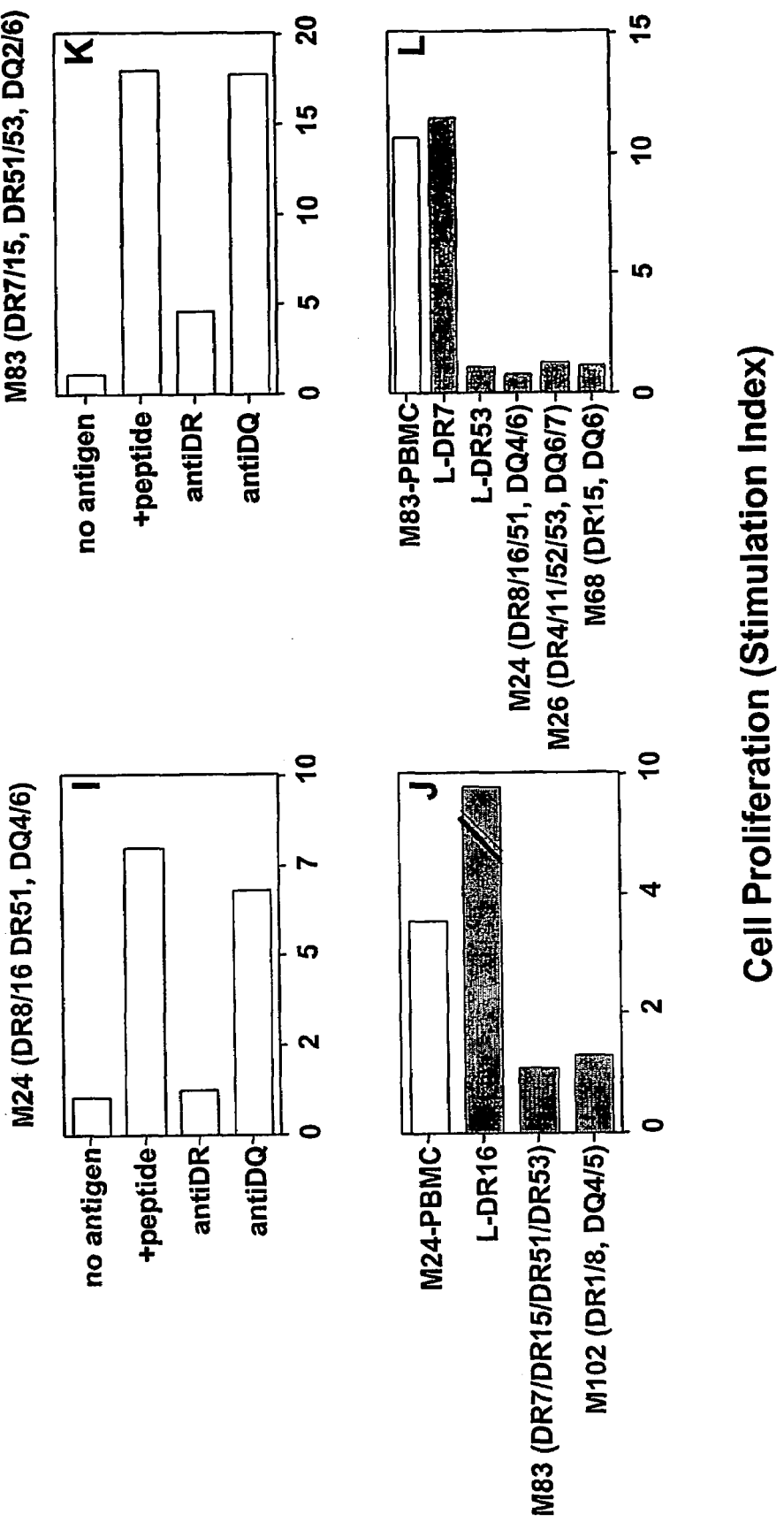
Figure 2 – page 3

EPSTEIN-BARR-VIRUS-SPECIFIC IMMUNIZATION

CROSS-REFERENCE TO RELATED APPLICATIONS

This application is a National Stage application under 35 U.S.C. § 371 and claims benefit under 35 U.S.C. § 119(a) of International Application No. PCT/US03/18682 having an International Filing Date of Jun. 13, 2003, which claims the benefit of priority of U.S. Provisional Application Ser. No. 60/388,625 having a filing date of Jun. 14, 2002.

STATEMENT AS TO FEDERALLY SPONSORED RESEARCH

This invention was made with government support under grant numbers R01CA80782, R01CA82677, M01-RR00585, and RR-00585, awarded by the National Institutes of Health. The government has certain rights in the invention.

TECHNICAL FIELD

This invention relates to materials and methods for preventing or treating post transplant lymphoproliferative disorders.

BACKGROUND

Epstein-Barr virus (EBV) is a lymphotropic gamma-herpesvirus that infects mostly B cells and is responsible for inducing their uncontrolled cell proliferation and transformation (Kieff (1996) in *Virology*, Fields, Knipe, and Howley, eds. Lipincott-Raven Publishers, New York, p. 2343). Under normal circumstances and in healthy individuals, EBV infections are not life threatening and generally are controlled by the immune system through the action of antigen-specific T-lymphocytes (Rickinson and Moss (1997) *Annu. Rev. Immunol.* 15:405). Both $CD8^+$ cytotoxic T lymphocytes (CTL) and $CD4^+$ helper T lymphocytes (HTL) can discriminate EBV-infected or EBV-transformed B cells and as a consequence, are able to inhibit their growth. EBV-specific T lymphocytes recognize antigen as molecular complexes formed by viral peptide epitopes with major histocompatibility complex (MHC) molecules, which are expressed on the surface of the infected/transformed B lymphocytes.

Although lifetime immunity to EBV apparently is achieved in normal individuals, the virus persists in a latent infection state (Nalesnik (1998) *Springer Semin. Immunopathol.* 20:325; Rowe (1999) *Front. Biosci.* 4:D346; and Babcock et al. (1998) *Immunity* 9:395), which effectively is controlled by EBV-specific T lymphocytes (Rickinson and Moss, supra). In immunosuppressed individuals such as transplant patients, however, primary EBV-infection usually results in post-transplant lymphoproliferative disorders (PTLD) that often progress into B-cell lymphomas (Hsieh et al. (1999) *Transpl. Infect. Dis.* 1:204; Hopwood and Crawford (2000) *J. Clin. Pathol.* 53:248; and Paya et al. (1999) *Transplantation* 68:1517). Current prophylactic and therapeutic approaches for PTLD and lymphomas are far from optimal.

SUMMARY

The invention provides compositions and articles of manufacture containing a peptide epitope that includes the amino acid sequence $EBNA2_{280-290}$ (SEQ ID NO:1) from the EBV EBNA2 antigen. This epitope is capable of inducing in vitro $CD4^+$ T cell responses to inhibit EBV-mediated B lymphocyte proliferation such as that associated with PTLD. T cell responses to the EBNA2 epitope are restricted by numerous MHC class II alleles (e.g., DR1, DR7, DR16, DR52, DQ2 and DQ7), indicating that this peptide is highly promiscuous and would be recognized by a large proportion (>50%) of the general population. T cells treated with the EBNA2 peptide epitope were able to recognize EBV-transformed lymphoblastoid cell lines and were efficient in inhibiting early B-cell proliferation induced by EBV infection. Thus, the invention provides the basis for a simple, inexpensive and widely applicable peptide-based vaccine to prevent and treat PTLD in solid organ transplant patients.

The invention also provides methods for using compositions containing the EBNA2 epitope. Specifically, the invention provides methods for using the EBNA2 peptide epitope to activate T cells and elicit an immune response against EBV in a subject. Compositions and methods of the invention are useful to, for example, treat subjects diagnosed with or at risk for lymphoproliferative diseases such as PTLD. The compositions and methods provided herein also can include immune enhancing agents.

As used herein, an immune enhancing agent is a substance that enhances the response of a T cell (e.g., a $CD4^+$ T cell or a $CD8^+$ T cell) to a stimulus delivered to the T cell via its antigen-specific T cell receptor (TCR). Immune enhancing agents include, for example, adjuvants, cytokines, and co-stimulatory molecules.

Adjuvants that can be used in any of the compositions and methods provided by the invention include, for example, cholera toxin (CT), *E. coli* heat labile toxin (LT), mutant CT (MCT; Yamamoto et al. (1997) *J. Exp. Med.* 185:1203-1210) and mutant LT (MLT; Di Tommaso et al. (1996) *Infect. Immunity* 64:974-979). MCT and MLT contain point mutations that substantially diminish toxicity without substantially compromising adjuvant activity relative to that of the parent molecules. Other useful adjuvants include alum, Freund's complete and incomplete adjuvants, and RIBI.

Cytokines and growth factors suitable for use in any of the compositions and methods of the invention include, without limitation, interleukin-1 (IL-1), IL-2, IL-3, IL-4, IL-6, IL-7, IL-12, IL-13, IL-15, interferon-γ (IFN-γ), tumor necrosis factor-α (TNF-α), granulocyte macrophage colony-stimulating factor (GM-CSF), and granulocyte-colony stimulating factor (G-CSF).

Co-stimulatory molecules that can be used in any of the compositions and methods provided herein include, for example, the B7 family of molecules (e.g., B7-1, B7-2, B7-H1, B7-H2, B7-H3, B7-H4, and 4-1BB ligand), as well as antibodies that bind to receptors for costimulatory molecules. Such receptors include CD28, CTLA-1, PD-1, ICOS, and 4-1BB.

It is understood that functional fragments, variants, or variants of functional fragments of any of the above immune enhancing agents can be used in the methods and compositions of the invention. All that is required is that the functional fragments, variants, or variants of functional fragments have at least 20% (e.g., at least 20%, 30%, 40%, 50%, 60%, 70%, 80%, 90%, 95%, 98%, 99%, 100%, or even more) of the activity of the corresponding immune enhancing agent. Functional fragments of polypeptide immune enhancing agents will be shorter than the corresponding, full-length, mature molecule and variants can contain additions, deletions, or substitutions of amino acids. While not required, substitutions typically are conservative substitutions.

An antigen-presenting cell (APC) can be essentially any cell that expresses a major histocompatibility class (MHC)

molecule. An APC can be, for example, a dendritic cell (DC), macrophage, monocyte, B cell, or a cell from a cell line (clonal or non-clonal) derived from any of these cells. As used herein, the terms "dendritic cells" and "DC" refer to inter-digitating DC. APC also can be any cell type (e.g., fibroblasts) transfected or transduced with and expressing a polynucleotide encoding an appropriate MHC molecule.

The invention provides compositions and methods that include an EBNA2 peptide epitope (EBNA2$_{280-290}$) containing the amino acid sequence Thr-Val-Phe-Tyr-Asn-Ile-Pro-Met-Pro-Leu as set forth in SEQ ID NO:1. It is noted, however, that EBNA2 peptide epitopes useful for the invention also can include up to 30 (e.g., 1, 2, 3, 4, 5, 6, 7, 8, 9, 10, 11, 12, 13, 14, 15, 18, 21, 24, 27, or 30) additional amino acids from the EBNA2 sequence, or from an unrelated sequence, at the amino terminus, the carboxy terminus, or both the amino terminus and the carboxy terminus of the EBNA2 sequence set forth in SEQ ID NO:1.

In the compositions, methods, and articles of manufacture provided herein, where the HLA class II molecules are DQ2 molecules, the relevant DQ2 molecules preferably are not DQA1*0501/DQB1*0201 molecules. Moreover, where the HLA class molecules are DQ7 molecules, the relevant DQ7 molecules preferably are not DQA1*0501/DQB1*0301 molecules. Since the EBV peptide epitope having the amino acid sequence set forth in SEQ ID NO:1 has been shown to be presented by a wide variety of HLA class II molecules, however, it is anticipated that the peptide epitope binds to and is presented by a large number of HLA molecules in addition to those disclosed herein. The invention thus is not limited to the HLA class II molecules disclosed herein. HLA class II molecules are known in the art (see, e.g., Marsh (2001) *Human Immunol.* 63:515-516).

The EBNA2$_{280-290}$ peptide epitope typically contains a motif (Phe-Tyr-Asn-Ile-Pro-Pro-Met-Pro-Leu; SEQ ID NO:6) that is predicted to bind to HLA class I molecules (e.g., HLA-A24 and HLA-Cw*0401). It therefore is understood that in the compositions, methods, and articles of manufacture of the invention, the relevant HLA molecules can be HLA class I molecules (e.g., HLA-A24 or HLA-Cw*0401) as well as HLA class II molecules.

The invention features a method for eliciting an immune response against EBV in a subject. The method can include identifying a subject in need of vaccination against EBV, wherein the subject expresses one or more HLA class II molecules selected from the group consisting of HLA-DR1, HLA-DR7, HLA-DR16, HLA-DR52, HLA-DQ2, and HLA-DQ7, and administering to the subject an EBV peptide epitope having the amino acid sequence set forth in SEQ ID NO:1. The method further can involve administering to the subject one or more immune-enhancing agents. The one or more immune-enhancing agents can include an adjuvant (e.g., Montanide ISA-51), a cytokine (e.g., GM-CSF), or a co-stimulatory molecule. The subject can have, be suspected of having, or be at risk for a PTLD.

In another aspect, the invention features a method for eliciting an immune response in a subject. The method can include administering to the subject (a) an EBV peptide epitope having the amino acid sequence set forth in SEQ ID NO:1, and (b) one or more immune-enhancing agents. The subject can express one or more HLA class II molecules selected from the group consisting of HLA-DR1, HLA-DR7, HLA-DR16, HLA-DR52, HLA-DQ2, and HLA-DQ7. The one or more immune-enhancing agents can include an adjuvant (e.g., Montanide ISA-51), a cytokine (e.g., GM-CSF), or a co-stimulatory molecule.

In yet another aspect, the invention features a method for activating a T cell (e.g., a CD4$^+$ T cell or a CD8$^+$ T cell). The method can include contacting the T cell with an EBV peptide epitope having the amino acid sequence set forth in SEQ ID NO:1, wherein the EBV peptide epitope is bound to an HLA class II molecule selected from the group consisting of HLA-DR1, HLA-DR7, HLA-DR16, HLA-DR52, HLA-DQ2, and HLA-DQ7. The contacting can be in vitro. Alternatively, the T cell can be in a subject (e.g., a human). Prior to the contacting, the EBV peptide epitope can be administered to the subject. The method can further involve administering to the subject one or more immune-enhancing agents. The one or more immune-enhancing agents can include an adjuvant (e.g., Montanide ISA-51), a cytokine (e.g., GM-CSF), or a co-stimulatory molecule.

The HLA class II molecule can be expressed on the surface of an APC containing a recombinant nucleotide sequence encoding the EBV peptide epitope. The contacting can be in vitro, or the T cell can be in a subject (e.g., a human). The method can further involve administering to the subject one or more immune-enhancing agents. The one or more immune-enhancing agents can include an adjuvant (e.g., Montanide ISA-51), a cytokine (e.g., GM-CSF), or a co-stimulatory molecule. Prior to the contacting, a nucleic acid containing the recombinant nucleotide sequence can be administered to the subject. The APC can be a cell, or a progeny of a cell, that has been returned to the subject after the steps of (a) removing from the subject a sample of cells comprising the cell or a precursor of the cell; and (b) transducing or transfecting the cell, or a precursor of the cell, with a nucleic acid containing the recombinant nucleotide sequence. The APC can be selected from the group consisting of a dendritic cell (i.e., an interdigitating dendritic cell), a macrophage, a monocyte, and a B lymphocyte. The APC can express, naturally or recombinantly, a co-stimulatory molecule (e.g., a co-stimulatory molecule selected from the group consisting of B7-1, B7-2, B7-H1, B7-H2, B7-H3, B7-H4, and 4-1BB ligand).

In another aspect, the invention features a composition that includes: (a) an EBV peptide epitope having the amino acid sequence set forth in SEQ ID NO:1; and (b) one or more immune-enhancing agents. The one or more immune-enhancing agents can include an adjuvant (e.g., Montanide ISA-51), a cytokine (e.g., GM-CSF), or a co-stimulatory molecule.

The invention also features a composition containing (a) a recombinant nucleic acid encoding an EBV peptide epitope having the amino acid sequence set forth in SEQ ID NO:1, and (b) a pharmaceutically acceptable carrier.

In another aspect, the invention features an article of manufacture. The article of manufacture can include: (a) an EBV peptide epitope having the amino acid sequence set forth in SEQ ID NO:1; and (b) a label or package insert indicating that the EBV peptide epitope can be (or is to be) administered to a subject in need of vaccination against EBV, wherein the subject expresses one or more HLA class II molecules selected from the group consisting of HLA-DR1, HLA-DR7, HLA-DR16, HLA-DR52, HLA-DQ2, and HLA-DQ7. It is understood that the label or package insert can indicate that the EBV peptide epitope can, in addition or alternatively, be used in any of the other methods described herein.

In yet another aspect, the invention features an ex vivo method for treating a lymphoproliferative disorder. The method can involve: (a) providing a population of cells including T cells; (b) activating the T cells in vitro with an EBV peptide epitope having the amino acid sequence set forth in SEQ ID NO:1; and (c) administering the activated T cells to a subject, wherein the subject has, is suspected to have, or is at risk for a lymphoproliferative disorder (e.g., PTLD). The population of T cells can be obtained from the subject.

Unless otherwise defined, all technical and scientific terms used herein have the same meaning as commonly understood by one of ordinary skill in the art to which this invention pertains. In case of conflict, the present document, including definitions, will control. Preferred methods and materials are described below, although methods and materials similar or equivalent to those described herein can be used in the practice or testing of the present invention. All publications, patent applications, patents and other references mentioned herein are incorporated by reference in their entirety. The materials, methods, and examples disclosed herein are illustrative only and not intended to be limiting.

Other features and advantages of the invention, e.g., inducing immune responses to EBV, will be apparent from the following description, from the drawings and from the claims.

DESCRIPTION OF DRAWINGS

FIGS. 2A-L are a series of bar graphs showing a human MHC class II molecule restriction analysis of the responses of various $EBNA2_{280-290}$-reactive T cell lines. Two different analyses were performed on each T cell line and are shown in separate graphs. Thus, for each T cell line there are two graphs. In the first analysis (FIGS. 2A, C, E, G, I, and K) the cells of the relevant T cell line were cultured in the presence of autologous APC and in either the absence of antigen ("no antigen") or in the presence of peptide with no antibody added ("+peptide") or with anti-DR ("antiDR") or anti-DQ ("antiDQ") added. In the graphs showing the data from the first analyses there are identifiers indicating the donor from which the relevant T cell line was obtained and MHC class II molecules expressed by these donors. In the second analysis (FIGS. 2B, D, F, H, J, and L), peptide-induced proliferative responses of the same T cell lines were studied using various MHC-typed APC. APC were PBMC, L cells transfected with and expressing cDNA encoding a human MHC molecule, or EBV transformed lymphoblastoid cell lines (LCL). On the y-axes of the graphs are shown which APC are used ("PBMC", "L" for L cells, and donor identifiers for LCL) and MHC class II molecules expressed by the APC. White bars represent determinations made using autologous APC and shaded bars determinations done with semi-allogeneic APC (i.e., APC sharing one allele of a relevant MHC molecule with the donor from which the relevant T cell line was made). The T cells used to obtain the data of the second analyses were those used in the corresponding first analysis graph immediately above the second analysis graph.

FIG. 5B shows the levels of IFN-γ produced by PBMC from donor M69 cultured with (hatched bars) or without (white bars) anti-CD3 antibody in the presence (1 or 10 μg/ml) or absence of CsA. FIG. 5C shows the levels of IFN-γ produced by $EBNA2_{280-290}$-specific T cells of a T cell line derived from donor M69 stimulated with autologous EBV-LCL (black bars) or control T2 cells (white bars) in the absence or presence (1 or 10 μg/ml) of CsA. Values are the means of triplicate determinations; error bars, SD.

DETAILED DESCRIPTION

Figure 1:
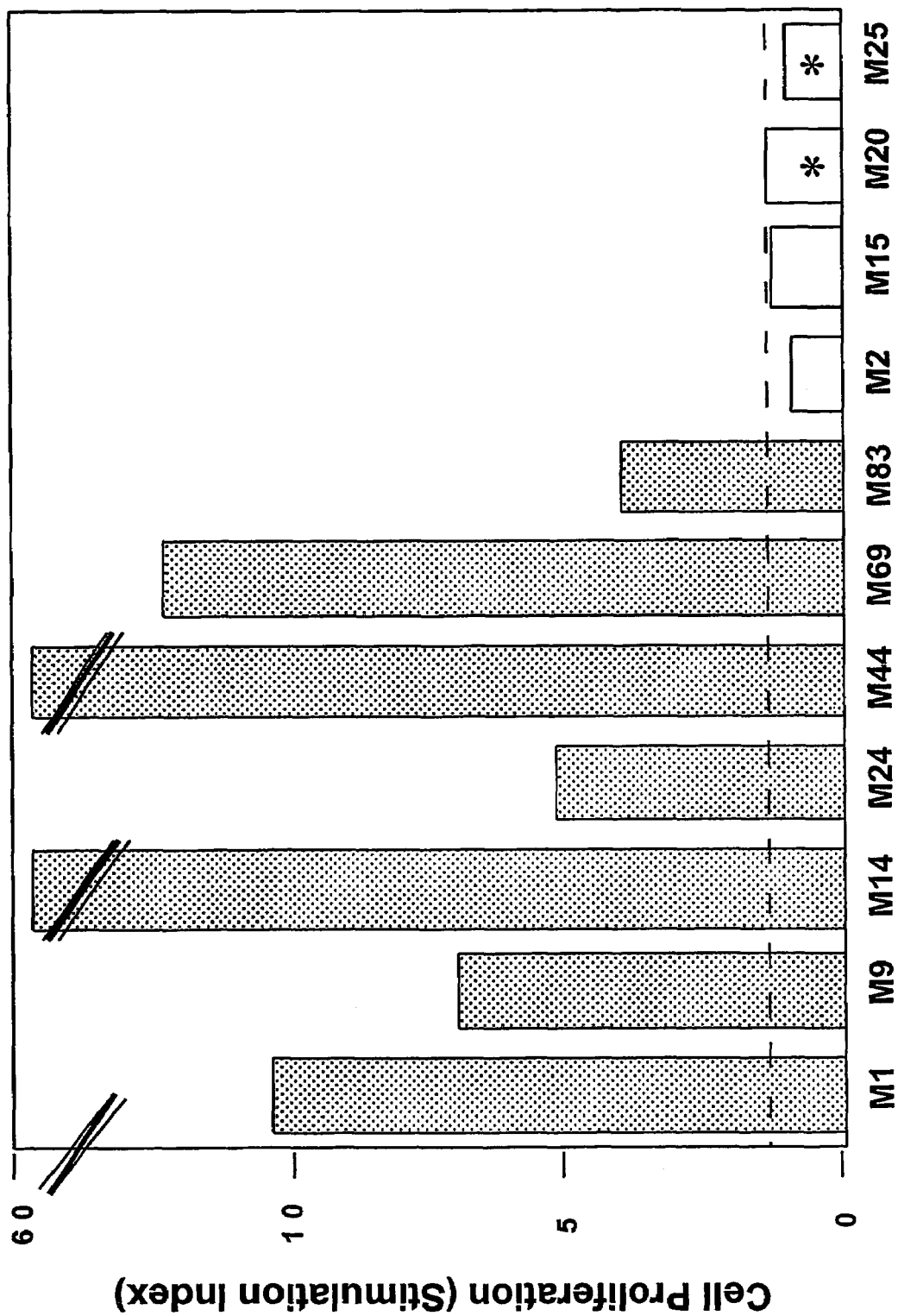
FIG. 1 is a bar graph showing the proliferative responses of various human T cell lines to a major histocompatibility complex (MHC) class II peptide ($EBNA2_{280-290}$) predicted to be promiscuous with respect to its ability to bind to human MHC class II molecules. Proliferative responses were measured by determining incorporation of [$^3$H]-thymidine into T cells cultured with and without $EBNA2_{280-290}$ in the presence of autologous irradiated antigen presenting cells (APC) (peripheral blood mononuclear cells; PBMC). Data ("Cell Proliferation") are presented as stimulation indices (SI), which were calculated by dividing the mean radioactivity (cpm) obtained in the presence of peptide by the mean radioactivity obtained in the absence of peptide. The donors of PBMC used to make the various T cell lines tested are indicated by the identifiers along the x-axis. Shaded bars correspond to proliferative responses with SI>3. White bars correspond to SI<3. The dashed line indicates a SI=1, where proliferation in the presence and absence of peptide was the same. Asterisks (*) indicate T cell lines that displayed a high background (non-specific) proliferative response. All determinations were done in triplicates and the standard deviations of all the means were less than 10% of the values of the mean.

The invention provides compositions and articles of manufacture containing peptide epitopes from the EBV EBNA2 antigen. These peptide epitopes are capable of inducing in vitro CD4$^+$ T cell responses that inhibit EBV-mediated B lymphocyte proliferation. Furthermore, the epitopes are highly promiscuous with respect to their ability to bind to MHC class II molecules, and are recognized by a large proportion (probably>50%) of the general population. T cells treated with an EBNA2 peptide epitope were able to recognize EBV-transformed lymphoblastoid cell lines and were efficient in inhibiting early B-cell proliferation induced by EBV infection. Thus, the invention provides a simple, inexpensive and widely applicable peptide-based vaccine to prevent and treat PTLD in solid organ transplant patients.

The invention also provides methods for using compositions containing EBNA2 epitopes. Specifically, the invention provides methods for using EBNA2 peptide epitopes to activate T cells and elicit an immune response against EBV in a subject. Compositions and methods of the invention are useful to, for example, treat subjects diagnosed with or at risk for lymphoproliferative diseases such as PTLD. The compositions and methods provided herein can include immune-enhancing agents.

1. EBV Peptide Epitopes

"Polypeptide," "protein," and "peptide" are used interchangeably herein, and refer to any peptide-linked chain of amino acids, regardless of post-translational modification (e.g., phosphorylation or glycosylation). While a peptide can be any length, those provided herein typically are about 10 to about 40 amino acid residues in length (e.g., 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 residues in length). As used herein, an "epitope" is a portion of an antigenic molecule (e.g., the EBV EBNA2 polypeptide) to which an antibody binds. Antigens can contain multiple epitopes. For polypeptide antigens, an epitope typically is about four to about 18 amino acids in length (e.g., six to 15, eight to 14, or nine to 13 amino acids in length). Two different T cell receptors (TCR) or antibodies can have the same epitope specificity if they bind to the same epitope or set of epitopes. The EBV EBNA2 peptide epitopes provided herein typically contain the amino acid sequence set forth in SEQ ID NO:1 (Thr-Val-Phe-Tyr-Asn-Ile-Pro-Pro-Met-Pro-Leu).

The EBNA2 peptide epitope can have an amino acid sequence that is a variant of the amino acid sequence set forth in SEQ ID NO:1, such that the amino acid sequence of the epitope contains an addition, deletion, or substitution at one or more positions relative to the amino acid sequence of SEQ ID NO:1. Amino acid substitutions useful in peptides of the invention can be conservative or non-conservative, but typically are conservative. Non-conservative substitutions may result in a substantial change in the hydrophobicity of the polypeptide or in the bulk of a residue side chain. In addition, non-conservative substitutions may make a substantial change in the charge of the polypeptide, such as reducing electropositive charges or introducing electronegative charges. Examples of non-conservative substitutions include a basic amino acid for a non-polar amino acid, or a polar amino acid for an acidic amino acid. Conservative amino acid substitutions replace an amino acid with an amino acid of the same class, whereas non-conservative amino acid substitutions replace an amino acid with an amino acid of a different class. Conservative amino acid substitutions typically have little effect on the structure or function of a polypeptide. Examples of conservative substitutions include amino acid substitutions within the following groups: glycine and alanine; valine, isoleucine, and leucine; aspartic acid and glutamic acid; asparagine, glutamine, serine, and threonine; lysine, histidine, and arginine; and phenylalanine and tyrosine. With respect to the amino acid sequence of the EBNA$_{280-290}$ peptide epitope, conservative substitutions include, without limitation: asparagine, glutamine, or serine at position 1; isoleucine or leucine at position 2; tyrosine at position 3; phenylalanine at position 4; glutamine, serine, or threonine at position 5; valine or leucine at position 6; and valine or isoleucine at position 11. One of skill in the art would appreciate that such substitutions could either diminish activity minimally or even result in a substantial increase in activity.

The EBNA2 peptide epitopes provided herein can contain EBNA2 sequences in additional to those set forth in SEQ ID NO:1, or can contain other amino acid sequences such as amino acid tags. A "tag" generally is a short amino acid sequence that provides a ready means of detection or purification through interactions with an antibody against the tag or through other compounds or molecules that recognize and bind to the tag. For example, tags such as c-myc, hemagglutinin, polyhistidine, or Flag® can be used to aid purification and detection of a polypeptide. As an example, a polypeptide with a polyhistidine tag can be purified based on the affinity of histidine residues for nickel ions (e.g., on a Ni-NTA column) or other metal ions, and can be detected in western blots by an antibody against polyhistidine (e.g., the Penta-His antibody; Qiagen, Valencia, Calif.). Tags can be inserted anywhere within the peptide sequence, although insertion at the amino- or carboxy-terminus is particularly useful.

The term "purified peptide" as used herein refers to a peptide that either has no naturally occurring counterpart (e.g., a peptidomimetic), or has been chemically or recombinantly synthesized and is thus uncontaminated by other peptides, or that has been separated or purified from other cellular components with which it is naturally accompanied (e.g., other cellular proteins, polynucleotides, or cellular components). Typically, a polypeptide is considered "purified" when it is at least 70%, by dry weight, free from the proteins and naturally occurring organic molecules with which it is naturally associated. A purified peptide of the invention therefore can be, for example, at least 80%, at least 90%, or at least 99%, by dry weight, the peptide of the invention.

Methods for producing purified peptides are well known in the art. By way of example and not limitation, purified polypeptides can be obtained by extraction from a natural source (e.g., from isolated cells, tissues or bodily fluids), by expression of a recombinant nucleic acid encoding the peptide, or by chemical synthesis. Suitable methods for purifying the polypeptides of the invention can include, for example, affinity chromatography, immunoprecipitation, size exclusion chromatography, and ion exchange chromatography. The extent of purification can be measured by any appropriate method, including but not limited to: column chromatography, polyacrylamide gel electrophoresis, or high-performance liquid chromatography.

Expression vectors that encode EBNA2 peptide epitopes of the invention can be used to produce the peptide epitopes to be purified. Expression systems that can be used for small or large scale production of the peptide epitopes of the invention include, but are not limited to, microorganisms such as bacteria (e.g., *E. coli* and *B. subtilis*) transformed with recombinant bacteriophage DNA, plasmid DNA, or cosmid DNA expression vectors containing the nucleic acid molecules that encode the peptide epitopes of the invention; yeast (e.g., *S. cerevisiae*) transformed with recombinant yeast expression vectors containing the nucleic acid molecules that encode the peptide epitopes of the invention; insect cell systems infected with recombinant virus expression vectors (e.g., baculovirus) containing the nucleic acid molecules that encode the peptide epitopes of the invention; plant cell systems infected with recombinant virus expression vectors (e.g., tobacco mosaic virus) or transformed with recombinant plasmid expression vectors (e.g., Ti plasmid) containing the nucleic acid molecules that encode the peptide epitopes of the invention; or mammalian cell systems (e.g., primary cells or immortalized cell lines such as COS cells, CHO cells, He La cells, HEK 293 cells, and 3T3 L1 cells) harboring recombinant expression constructs containing promoters derived from the genome of mammalian cells (e.g., the metallothionein promoter) or from mammalian viruses (e.g., the adenovirus late promoter and the cytomegalovirus promoter), along with the nucleic acids that encode the peptide epitopes of the invention.

The EBNA2 peptide epitopes useful in the invention can be EBNA2 peptide epitopes recognized by an effector T cell or a precursor of an effector T cell when the peptide epitope is complexed with an MHC molecule. The invention is not limited by: (a) the T cell having any particular phenotype (e.g., $CD4^+$ or $CD8^+$) or function (e.g., cytotoxicity, helper activity, immune deviating activity, or suppressive activity); or (b) the MHC being of any particular class. While the majority of T cells with cytotoxic activity are $CD8^+$ and recognize peptide epitopes bound to MHC class I molecules, $CD4^+$ CTL that recognize antigenic peptides bound to MHC class II molecules are known in the art (e.g., those described in Example 7). $CD4^+$ CTL that recognize peptides bound to MHC class I molecules and $CD8^+$ CTL that recognize antigenic peptides bound to MHC class II molecules have also been described. In addition, while the majority of T cells with helper and/or immune deviating activity are $CD4^+$ T cells and recognize antigenic peptides bound to MHC class II molecules, these activities have also been observed in MHC class I restricted $CD8^+$ T cells. Similarly, while most immunosuppressive T cells are $CD8^+$ T cells, $CD4^+$ T cells with immunosuppressive activity have also been demonstrated. The invention includes peptide epitopes recognized by all these T cells. Preferred peptide epitopes will be those recognized MHC class II restricted $CD4^+$ helper/cytotoxic T cells.

2. Nucleic Acids, Vectors, and Host Cells

The invention provides isolated nucleic acid molecules that encode polypeptides containing the EBV EBNA2 peptide epitope set forth in SEQ ID NO:1. In some embodiments, the isolated nucleic acids encode polypeptides containing (1) the EBNA2 amino acid sequence set forth in SEQ ID NO:1 and (2) additional amino acid sequences, either from EBNA2 or from other polypeptides or amino acid tags. As used herein, "nucleic acid" refers to both RNA and DNA, including cDNA, genomic DNA, and synthetic (e.g., chemically synthesized) DNA. The nucleic acid can be double-stranded or single-stranded (i.e., a sense or an antisense single strand). The term "isolated" as used herein with reference to a nucleic acid refers to a naturally-occurring nucleic acid that is not immediately contiguous with both of the sequences with which it is immediately contiguous (one at the 5' end and one at the 3' end) in the naturally-occurring genome of the organism from which it is derived. The term "isolated" as used herein with respect to nucleic acids also includes any non-naturally-occurring nucleic acid sequence, since such non-naturally-occurring sequences are not found in nature and do not have immediately contiguous sequences in a naturally-occurring genome.

An isolated nucleic acid can be, for example, a DNA molecule, provided one of the nucleic acid sequences that is normally immediately contiguous with the DNA molecule in a naturally-occurring genome is removed or absent. Thus, an isolated nucleic acid includes, without limitation, a DNA molecule that exists as a separate molecule (e.g., a chemically synthesized nucleic acid, or a cDNA or genomic DNA fragment produced by PCR or restriction endonuclease treatment) independent of other sequences as well as DNA that is incorporated into a vector, an autonomously replicating plasmid, a virus (e.g., a retrovirus, lentivirus, adenovirus, or herpes virus), or into the genomic DNA of a prokaryote or eukaryote. In addition, an isolated nucleic acid can include an engineered nucleic acid such as a recombinant DNA molecule that is part of a hybrid or fusion nucleic acid. A nucleic acid existing among hundreds to millions of other nucleic acids within, for example, cDNA libraries or genomic libraries, or gel slices containing a genomic DNA restriction digest, is not considered an isolated nucleic acid.

Isolated nucleic acids of the invention contain sequences encoding the EBNA2 peptide epitopes of the invention. The nucleic acids may contain sequences identical to those encoding a wild-type EBNA2 polypeptide. Alternatively, the nucleic acids can contain codons other than the wild-type codons that, due to the degeneracy of the genetic code, encode EBNA2 polypeptides identical to the wild-type polypeptide.

Nucleic acids of the invention can contain coding sequences for EBNA2 polypeptides coupled to sequences that encode one or more additional peptides or tags. Furthermore, the coding sequences can be linked in frame and inserted into a suitable expression vector, such that one polypeptide results from transcription and translation of the coding sequences. For example, the nucleic acids of the invention may include coding sequences from both EBNA2 and a second polypeptide, linked in such a way that a single polypeptide is produced. Additionally, nucleic acids of the invention can encode EBNA2 peptides coupled to one or more suitable tags such as those described above.

The isolated nucleic acid molecules provided herein can be produced by standard techniques, including, without limitation, common molecular cloning and chemical nucleic acid synthesis techniques. For example, polymerase chain reaction (PCR) techniques can be used to obtain an isolated nucleic acid molecule encoding an EBNA2 peptide epitope. Isolated nucleic acids of the invention also can be chemically synthesized, either as a single nucleic acid molecule (e.g., using automated DNA synthesis in the 3' to 5' direction using phosphoramidite technology) or as a series of polynucleotides. For example, one or more pairs of polynucleotides (e.g., >30 nucleotides) can be synthesized that contain the desired sequence, with each pair containing a short segment of complementarity (e.g., about 15 nucleotides) such that a duplex is formed when the polynucleotide pair is annealed. DNA polymerase is used to extend the polynucleotides, resulting in a single, double-stranded nucleic acid molecule per polynucleotide pair.

The invention also provides vectors containing the nucleic acids described above. As used herein, a "vector" is a replicon, such as a plasmid, phage, or cosmid, into which another DNA segment may be inserted so as to bring about the replication of the inserted segment. The vectors of the invention are preferably expression vectors, in which the nucleotides encode the EBNA2 peptide epitopes of the invention with an initiator methionine, operably linked to expression control sequences. As used herein, "operably linked" means incorporated into a genetic construct so that expression control sequences effectively control expression of a coding sequence of interest. An "expression control sequence" is a DNA sequence that controls and regulates the transcription and translation of another DNA sequence, and an "expression vector" is a vector that includes expression control sequences, so that a relevant DNA segment incorporated into the vector is transcribed and translated. A coding sequence is "operably linked" and "under the control" of transcriptional and translational control sequences in a cell when RNA polymerase transcribes the coding sequence into mRNA, which then is translated into the protein encoded by the coding sequence.

Methods well known to those skilled in the art may be used to subclone isolated nucleic acid molecules encoding polypeptides of interest into expression vectors containing relevant coding sequences and appropriate transcriptional/translational control signals. See, for example, Sambrook et al., *Molecular Cloning: A Laboratory Manual* ($2^{nd}$ edition), Cold Spring Harbor Laboratory, New York (1989); and Ausuble et al., *Current Protocols in Molecular Biology*, Green Publishing Associates and Wiley Interscience, New York (1989). Expression vectors of the invention can be used in a variety of systems (e.g., bacteria, yeast, insect cells, and mammalian cells), as described above. Examples of suitable expression vectors include, without limitation, plasmids and viral vectors derived from, for example, herpes viruses, retroviruses, vaccinia viruses, adenoviruses, and adeno-associated viruses. A wide variety of suitable expression vectors and systems are commercially available, including the pET series of bacterial expression vectors (Novagen, Madison, Wis.), the Adeno-X expression system (Clontech), the Baculogold baculovirus expression system (BD Biosciences Pharmingen, San Diego, Calif.), and the pCMV-Tag vectors (Stratagene, La Jolla, Calif.).

An expression vector can include a nucleotide sequence encoding a tag sequence designed to facilitate subsequent manipulation of the expressed nucleic acid sequence (e.g., purification or localization). Tag sequences, such as green fluorescent protein (GFP), glutathione S-transferase (GST), polyhistidine, c-myc, hemagglutinin, or Flag™ tag (Kodak, New Haven, Conn.) sequences typically are expressed as a fusion with the encoded polypeptide. Such tags can be inserted anywhere within the polypeptide including at either the carboxyl or amino terminus.

The invention also provides host cells containing vectors of the invention. The term "host cell" is intended to include prokaryotic and eukaryotic cells into which a recombinant expression vector can be introduced. As used herein, "transformed" and "transfected" encompass the introduction of a nucleic acid molecule (e.g., a vector) into a cell by one of a number of techniques. Although not limited to a particular technique, a number of these techniques are well established within the art. Prokaryotic cells can be transformed with nucleic acids by, for example, electroporation or calcium chloride mediated transformation. Nucleic acids can be transfected into mammalian cells by techniques including, for example, calcium phosphate co-precipitation, DEAE-dextran-mediated transfection, lipofection, electroporation, or microinjection. Suitable methods for transforming and transfecting host cells are found in Sambrook et al., *Molecular Cloning: A Laboratory Manual* ($2^{nd}$ edition), Cold Spring Harbor Laboratory, New York (1989), and reagents for transformation and/or transfection are commercially available (e.g., Lipofectin® (Invitrogen/Life Technologies); Fugene (Roche, Indianapolis, Ind.); and SuperFect (Qiagen)).

3. Methods of Activating an Immune Response

The invention features methods of activating mammalian immune responses in which cells of the immune system are exposed to one or more of the EBNA2 peptide epitopes provided herein. The peptide epitopes of the invention can generate MHC class I and class II restricted T cell responses. For example, the EBNA2 peptide epitope can be bound to an HLA class II molecule selected from the group consisting of HLA-DR1, LA-DR7, HLA-DR16, HLA-DR52, HLA-DQ2, and HLA-DQ7. Where the HLA class molecules are DQ2 molecules, however, the relevant DQ2 molecules preferably are not DQA1*0501/DQB1*0201 molecules. In addition, where the HLA class molecules are DQ7 molecules, the relevant DQ7 molecules preferably are not DQA1*0501/DQB1*0301 molecules.

Methods of the invention can be performed in vitro, in vivo, or ex vivo. In vitro application of the EBNA2 peptide epitope can be useful, for example, in basic scientific studies of immune mechanisms or for production of activated T cells for use in either studies on T cell function or, for example, passive immunotherapy. The peptide epitopes (or compositions containing them) also can be used as "positive controls" to test for EBV-specific T cells (e.g., in diagnostic assays). The methods provided herein can be applied to a wide range of species, e.g., humans, non-human primates (e.g., monkeys), horses, cattle, pigs, sheep, goats, dogs, cats, rabbits, guinea pigs, hamsters, rats, and mice.

In the in vitro methods of the invention, T cells ($CD4^+$ and/or $CD8^+$) obtained from a mammalian subject are cultured with an EBNA2 peptide epitope of the invention and antigen presenting cells (APC), preferably, but not necessarily, obtained from the same individual as the T cells. Where the APC are obtained from a different individual, the donor of the T cells and the donor of the APC will preferably express at least one major histocompatibility complex (MHC) molecule (e.g., a MHC class II molecule) in common. APC can be essentially any MHC molecule-expressing cell. Where it is desired to elicit a MHC class I restricted immune response, the APC will express MHC class I molecules (and optionally MHC class II molecules) and where it is desired to elicit an MHC class II restricted immune response, the APC will express MHC class II molecules (and optionally MHC class I molecules). The APC may also express one or more co-stimulatory molecules, e.g., the B7 family of molecules. Thus APC can be, for example, interdigitating DC, macrophages, monocytes, B cells, or cell lines (clonal or non-clonal) derived from any of these cells. They also can be any cell type (e.g., fibroblasts) transfected or transduced with and expressing a polynucleotide encoding an appropriate MHC molecule. Such cultures can also be supplemented with one or more cytokines or growth factors such as, without limitation, IL-1, IL-2, IL-3, IL-4, IL-6, IL-7, IL-12, IL-13, IL-15, IFN-γ, TNF-α, GM-CSF, or G-CSF. The cultures can be "re-stimulated" as often as necessary with the peptide epitope. The cultures also can be monitored at various times to ascertain whether the desired level of immune reactivity (e.g., CTL activity) has been attained.

The EBV EBNA2 peptide epitopes of the invention generally are useful for generating immune responses and as prophylactic vaccines or immune response-stimulating therapeutics. Thus, they can be used, for example, as vaccines or therapeutic agents against infectious diseases due to any of the pathogens listed herein. As used herein, "prophylaxis" can mean complete prevention of the symptoms of a disease (e.g., PTLD), a delay in onset of the symptoms of a disease, or a lessening in the severity of subsequently developed disease symptoms. "Prevention of the symptoms of a disease" means that symptoms of the disease are essentially absent. As used herein, "therapy" can mean a complete abolishment of the symptoms of a disease or a decrease in the severity of the symptoms of the disease.

It is understood that while the responses generated by the EBNA2 peptide epitopes of the invention are preferably prophylactic and/or therapeutic, it is not absolutely required that they be. For example, the EBNA2 epitopes can be used in basic scientific studies on immune responses that are neither prophylactic nor therapeutic or, for example, as "positive controls" in assays of T cell responsiveness to EBV or EBNA2.

The invention is not limited by the mechanisms by which the EBNA2 peptide epitopes exert prophylactic and/or therapeutic effects. In that they activate CD4+ T cells, prophylactic and/or therapeutic effects could be due to, for example, the action of CD4+ cytotoxic T lymphocytes, cytokines that are produced by CD4+ T cells but are active on other effector cells (e.g., macrophages, monocytes, or granulocytes), or antibodies produced by B cells whose responsiveness is dependent on CD4+ T cell "helper" activity.

For in vivo approaches, a therapeutically effective amount of an EBNA2 peptide epitope is administered directly to a subject. Typically, the EBNA2 peptide epitope is suspended in a pharmaceutically-acceptable carrier. Pharmaceutically acceptable carriers are biologically compatible vehicles (e.g., physiological saline) that are suitable for administration to a human or other mammalian subject. A therapeutically effective amount is an amount of the peptide epitope that is capable of producing a medically desirable result (e.g., a T cell response) in a treated animal. An EBNA2 peptide epitope can be administered orally or transdermally or injected (or infused) intravenously (i.v.), subcutaneously, intramuscularly, intraperitoneally, intrarectally, intravaginally, intranasally, intragastrically, intratracheally, or intrapulmonarily. The peptide epitope can be delivered directly to an appropriate lymphoid tissue (e.g., spleen, lymph node, or mucosal-associated lymphoid tissue). The dosage require for a particular subject depends upon many factors, including the subject's size, body surface area, age, the particular compound to be administered, sex, time and route of administration, general health, and other drugs being administered concurrently. Suitable dosages typically are in the range of 0.001-10.0 mg/kg. Wide variations in the needed dosage are to be expected in view of the differing efficiencies of various routes of administration. For example, oral administration would be expected to require higher dosages than administration by i.v. injection. Variations in dosage levels can be adjusted using standard empirical routines for optimization as is well understood in the art. Administration can be single or multiple (e.g., 2- or 3-, 4-, 6-, 8-, 10-, 20-, 50-, 100-, 150-, or more fold). Encapsulation of the peptide epitope in a suitable delivery vehicle (e.g., polymeric microparticles or implantable devices) may increase the efficiency of delivery, particularly for oral delivery.

Alternatively, a nucleic acid molecule containing a nucleic acid sequence that encodes an EBNA2 peptide epitope of interest can be delivered to an appropriate cell of the animal. Expression of the coding sequence preferably will be directed to lymphoid tissue of the subject by, for example, delivery of the polynucleotide to the lymphoid tissue. In one embodiment, this can be achieved using a polymeric, biodegradable microparticle or microcapsule delivery vehicle sized to optimize phagocytosis by phagocytic cells such as macrophages. PLGA (poly-lacto-co-glycolide) microparticles approximately 1-10 μm in diameter can be used, for example. The polynucleotide is encapsulated in these microparticles, which are taken up by macrophages and gradually biodegraded within the cell, thereby releasing the polynucleotide. Once released, the DNA is expressed within the cell. A second type of microparticle is intended not to be taken up directly by cells, but rather to serve primarily as a slow-release reservoir of nucleic acid that is taken up by cells only upon release from the micro-particle through biodegradation. These polymeric particles should therefore be large enough to preclude phagocytosis (i.e., larger than 5 μm and preferably larger than 20 μm).

Another method for achieving uptake of nucleic acid molecules is to use liposomes, which can be prepared by standard methods. Vectors can be incorporated alone into these delivery vehicles or can be co-incorporated with tissue-specific antibodies. Alternatively, one can prepare a molecular conjugate composed of a plasmid or other vector attached to poly-L-lysine by electrostatic or covalent forces. Poly-L-lysine binds to a ligand that can bind to a receptor on target cells (Cristiano et al. (1995) *J. Mol. Med.* 73:479). Alternatively, lymphoid tissue specific targeting can be achieved by the use of lymphoid tissue-specific transcriptional regulatory elements (TRE) such as a B lymphocyte, T lymphocyte, or dendritic cell specific TRE. Lymphoid tissue specific TRE are known (see, e.g., Thompson et al. (1992) *Mol. Cell. Biol.* 12:1043-1053; Todd et al. (1993) *J. Exp. Med.* 177:1663-1674; Penix et al. (1993) *J. Exp. Med.* 178:1483-1496). Delivery of "naked DNA" (i.e., without a delivery vehicle) to an intramuscular, intradermal, or subcutaneous site is another means by which to achieve in vivo expression.

As for peptides, nucleic acid molecules can be administered with a pharmaceutically acceptable carrier. Dosages will vary, but a typical dosage for administration of nucleic acid molecule is from about $10^6$ to about $10^{12}$ copies of the nucleic acid molecule. Doses can be repeatedly administered. Routes of administration can be any of those listed above.

EBNA2 peptide epitopes also can be administered using ex vivo methods. In one ex vivo approach, lymphoid cells, including T cells (CD4$^+$ and/or CD8$^+$ T cells), are isolated from a subject and exposed to a peptide epitope in vitro (see above). The lymphoid cells can be exposed one time or multiple times (e.g., 2, 3, 4, 6, 8, or 10 times). The level of immune activity (e.g., CTL activity) in the lymphoid cells can be tested after one or more exposures to the epitope. Once the desired activity and level of that activity is attained, the cells are reintroduced into the subject via any of the routes listed herein. The therapeutic or prophylactic efficacy of such an ex vivo approach is dependent on the ability of the ex vivo activated lymphocytes to exert, directly or indirectly, a neutralizing or cytotoxic effect on, for example, EBV or host cells infected with EBV.

An alternative ex vivo strategy can involve transfecting or transducing cells obtained from a subject with a nucleic acid molecule encoding an EBNA2 peptide epitope. The transfected or transduced cells then are returned to the subject. While such cells typically would be lymphoid cells, they also could be any of a wide range of types including, without limitation, fibroblasts, bone marrow cells, macrophages, monocytes, dendritic cells, epithelial cells, endothelial cells, keratinocytes, or muscle cells that act as a source of the peptide epitope for as long as they survive in the subject. The use of lymphoid cells would be particularly advantageous in that such cells would be expected to home to lymphoid tissue (e.g., lymph nodes or spleen) and thus the peptide epitope would be produced in high concentration at the site where they exert their effect (i.e., activation of an immune response). By using this approach, as for the above-described in vivo approach using nucleic acid molecules encoding EBNA2 peptide epitopes, active in vivo immunization with the epitope is achieved. The same genetic constructs and signal sequences described for the in vivo approach can be used for this ex vivo strategy.

The above ex vivo method can include the steps of harvesting cells from a subject, culturing the cells, transducing them with an expression vector, and maintaining the cells under conditions suitable for expression of the EBNA2 peptide epitope. Such methods are known in the art. The transduction step can be accomplished by any standard means used for ex vivo gene therapy, including calcium phosphate-mediated transfection, lipofection, electroporation, viral infection, and biolistic gene transfer. Alternatively, liposomes or polymeric microparticles can be used. Cells that have been successfully transduced are then selected for expression of the peptide epitope or expression of a drug resistance gene. If desired, the cells can be treated with an agent (e.g., x- or y-irradiation or mitomycin C) that inhibits cell proliferation; generally where the cells are cancer cells (particularly cancer cells from the subject or from an individual that is MHC identical to the subject) will be so treated. The cells are then injected or implanted into the patient.

Methods for testing whether a peptide epitope is therapeutic for or prophylactic against a PTLD are known in the art. Where a therapeutic effect is being tested, a test population displaying symptoms of the disease (e.g., B cell lymphoma) is treated with a test peptide epitope, using any of the above described strategies. A control population, also displaying symptoms of the disease, is treated, using the same methodology, with a placebo. Disappearance or a decrease of the disease symptoms in the test subjects would indicate that the peptide epitope was an effective therapeutic agent.

By applying the same strategies to subjects prior to onset of disease symptoms (e.g., subjects who will undergo soft tissue transplant or who are otherwise considered to be likely candidates for development of PTLD, or experimental animals in which an appropriate disease spontaneously arises or can be deliberately induced, EBV peptide epitopes can be tested for efficacy as prophylactic agents, i.e., vaccines.

4. Compositions

The invention provides compositions containing the EBV peptide epitopes described herein (e.g., the $EBNA2_{280-290}$ epitope). Such compositions are suitable for administration to a subject to potentiate an anti-EBV immune response, and thus can be used to prevent or treat PTLD. In addition, the invention provides compositions containing nucleic acid molecules encoding EBV peptide epitopes such as the $EBNA2_{280-290}$ epitope.

Methods for formulating and subsequently administering therapeutic compositions are well known to those skilled in the art. Dosages typically are dependent on the responsiveness of the subject to the molecule, with the course of treatment lasting from several days to several months, or until a suitable immune response is achieved. Persons of ordinary skill in the art routinely determine optimum dosages, dosing methodologies and repetition rates. As described above, dosages can vary depending on the relative potency of the epitope and the method of administration. Compositions containing the molecules provided herein may be given once or more daily, weekly, monthly, or even less often.

In addition to the peptide epitopes and nucleic acids encoding peptide epitopes, compositions of the invention further can contain immune enhancing agents that will facilitate an immune response. Suitable immune enhancing agents include, for example, adjuvants (e.g., CT, LT, MCT, MLT, alum, Freund's complete and incomplete adjuvants, and RIBI), cytokines (e.g., IL-1, IL-2, IL-3, IL-4, IL-6, IL-7, IL-12, IL-13, IL-15, IFN-γ, TNF-α, GM-CSF, and G-CSF), and co-stimulatory molecules (e.g., B7-1, B7-2, B7-H1, B7-H2, B7-H3, B7-H4, 4-1BB ligand, and antibodies that bind to receptors for costimulatory molecules such as CD28, CTLA-1, PD-1, ICOS, and 4-1BB).

Compositions of the invention can contain peptides and/or nucleic acids that are admixed, encapsulated, conjugated or otherwise associated with other molecules, molecular structures, or mixtures of compounds such as, for example, liposomes, receptor targeted molecules, or oral, topical or other formulations for assisting in uptake, distribution and/or absorption.

As described above, pharmaceutically acceptable carriers are pharmaceutically acceptable solvents, suspending agents, or any other pharmacologically inert vehicles for delivering antibodies to a subject. Pharmaceutically acceptable carriers can be liquid or solid, and can be selected with the planned manner of administration in mind so as to provide for the desired bulk, consistency, and other pertinent transport and chemical properties, when combined with one or more therapeutic compounds and any other components of a given pharmaceutical composition. Typical pharmaceutically acceptable carriers include, without limitation: water; saline solution; binding agents (e.g., polyvinylpyrrolidone or hydroxypropyl methylcellulose); fillers (e.g., lactose and other sugars, gelatin, or calcium sulfate); lubricants (e.g., starch, polyethylene glycol, or sodium acetate); disintegrates (e.g., starch or sodium starch glycolate); and wetting agents (e.g., sodium lauryl sulfate).

Pharmaceutical compositions containing molecules provided herein can be administered by a number of methods, depending upon whether local or systemic treatment is desired. Administration can be, for example, parenteral (e.g., by subcutaneous, intrathecal, intraventricular, intramuscular, or intraperitoneal injection, or by intravenous drip); oral; topical (e.g., transdermal, sublingual, ophthalmic, or intranasal); or pulmonary (e.g., by inhalation or insufflation of powders or aerosols). Administration can be rapid (e.g., by injection) or can occur over a period of time (e.g., by slow infusion or administration of slow release formulations). For administration to the central nervous system, antibodies can be injected or infused into the cerebrospinal fluid, typically with one or more agents capable of promoting penetration across the blood-brain barrier.

Compositions and formulations for parenteral, intrathecal or intraventricular administration include sterile aqueous solutions (e.g., sterile physiological saline), which also can contain buffers, diluents and other suitable additives (e.g., penetration enhancers, carrier compounds and other pharmaceutically acceptable carriers).

Compositions and formulations for oral administration include, for example, powders or granules, suspensions or solutions in water or non-aqueous media, capsules, sachets, or tablets. Such compositions also can incorporate thickeners, flavoring agents, diluents, emulsifiers, dispersing aids, or binders.

Formulations for topical administration include, for example, sterile and non-sterile aqueous solutions, non-aqueous solutions in common solvents such as alcohols, or solutions in liquid or solid oil bases. Such solutions also can contain buffers, diluents and other suitable additives. Pharmaceutical compositions and formulations for topical administration can include transdermal patches, ointments, lotions, creams, gels, drops, suppositories, sprays, liquids, and powders. Conventional pharmaceutical carriers, aqueous, powder or oily bases, thickeners and the like may be useful.

Pharmaceutical compositions include, but are not limited to, solutions, emulsions, aqueous suspensions, and liposome-containing formulations. These compositions can be generated from a variety of components that include, for example, preformed liquids, self-emulsifying solids and self-emulsifying semisolids. Emulsion formulations are particularly useful for oral delivery of therapeutic compositions due to their ease of formulation and efficacy of solubilization, absorption, and bioavailability. Liposomes can be particularly useful due to their specificity and the duration of action they offer from the standpoint of drug delivery.

Molecules of the invention can encompass any pharmaceutically acceptable salts, esters, or salts of such esters, or any other compound which, upon administration to a subject, is capable of providing (directly or indirectly) the biologically active metabolite or residue thereof. Accordingly, for example, the invention provides pharmaceutically acceptable salts of peptides (e.g., EBNA2 peptide epitopes such as $EBNA2_{280-290}$), prodrugs and pharmaceutically acceptable salts of such prodrugs, and other bioequivalents. A prodrug is a therapeutic agent that is prepared in an inactive form and is converted to an active form (i.e., drug) within the body or cells thereof by the action of endogenous enzymes or other chemicals and/or conditions. The term "pharmaceutically acceptable salts" refers to physiologically and pharmaceutically acceptable salts of the EBNA2 peptide epitopes useful in methods of the invention (i.e., salts that retain the desired biological activity of the EBNA2 peptide epitopes without imparting undesired toxicological effects). Examples of pharmaceutically acceptable salts include, but are not limited to, salts formed with cations (e.g., sodium, potassium, calcium, or polyamines such as spermine); acid addition salts formed with inorganic acids (e.g., hydrochloric acid, hydrobromic acid, sulfuric acid, phosphoric acid, or nitric acid); salts formed with organic acids (e.g., acetic acid, citric acid, oxalic acid, palmitic acid, or fumaric acid); and salts formed with elemental anions (e.g., bromine, iodine, or chlorine).

Compositions additionally can contain other adjunct components conventionally found in pharmaceutical compositions. Thus, the compositions also can include compatible, pharmaceutically active materials such as, for example, antipruritics, astringents, local anesthetics or anti-inflammatory agents, or additional materials useful in physically formulating various dosage forms of the compositions of the present invention, such as dyes, flavoring agents, preservatives, antioxidants, opacifiers, thickening agents, and stabilizers. Furthermore, the composition can be mixed with auxiliary agents, e.g., lubricants, preservatives, stabilizers, wetting agents, emulsifiers, salts for influencing osmotic pressure, buffers, colorings, flavorings, penetration enhancers, and aromatic substances. When added, however, such materials should not unduly interfere with the biological activities of the peptide or nucleic acid components within the composition.

The compositions provided herein, which can be presented conveniently in unit dosage form, can be prepared according to conventional techniques well known in the pharmaceutical industry. Such techniques include the step of bringing into association the active ingredients (i.e., the peptide epitopes or nucleic acid molecules encoding the peptide epitopes) with the desired pharmaceutical carrier(s). Typically, the formulations can be prepared by uniformly and intimately bringing the active ingredients into association with liquid carriers or finely divided solid carriers or both, and then, if necessary, shaping the product. Formulations can be sterilized if desired, provided that the method of sterilization does not interfere with the effectiveness of the peptides or nucleic acids contained in the formulation.

Compositions of the present invention can be formulated into any of many possible dosage forms such as, without limitation, tablets, capsules, liquid syrups, soft gels, suppositories, and enemas. Compositions also can be formulated as suspensions in aqueous, non-aqueous or mixed media. Aqueous suspensions further can contain substances that increase the viscosity of the suspension including, for example, sodium carboxymethyl-cellulose, sorbitol, and/or dextran. Suspensions also can contain stabilizers.

5. Articles of Manufacture

EBV peptide epitopes of the invention can be combined with packaging material and sold as kits for moderating immune responses and preventing or treating PTLD. Components and methods for producing articles of manufacture such as kits are well known. An article of manufacture may include one or more of the EBV EBNA2 peptide epitopes set out in the above sections. In addition, the article of manufacture further may include buffers or other solutions necessary to effect modulation of an immune response. Instructions describing how the EBNA2 peptide epitopes are useful for moderating anti-EBV immune responses and preventing or treating PTLD can be included in such kits.

Alternatively, an article of manufacture can contain a nucleic acid molecule (e.g., a vector containing a nucleic acid sequence encoding an EBNA2 peptide epitope, operably linked to expression control sequences). Such an article of manufacture can include instructions for using the nucleic acid molecule to produce an EBNA2 peptide and/or to moderate immune responses and prevent or treat PTLD. In addition, an article of manufacture can include any components necessary to achieve production of an EBNA2 peptide and/or moderation of immune responses. In another embodiment, an article of manufacture can contain host cells that contain nucleic acid molecules useful for producing EBNA2 peptide epitopes.

The invention will be further described in the following examples, which do not limit the scope of the invention described in the claims.

EXAMPLES

Example 1

Materials and Methods

Cell lines: EBV-tansformed lymphoblastoid cell lines (EBV-LCL) were generated from peripheral blood mononuclear cells of HLA-typed volunteers using culture supernatant from the EBV-producing B95-8 cell line (American Type Culture Collection (ATCC), Manassas, Va.). Mouse fibroblast cell lines (L-cells) transfected and expressing individual human MHC class II molecules were provided by R. W. Karr (Park-Davis, Ann Arbor, Mo.).

Synthetic peptides and epitope prediction analysis: Potential MHC class II promiscuous helper T cell epitopes were predicted from the amino acid sequence of the EBNA2 antigen using the algorithm tables for three HLA-DR alleles (DRB1*0101, DRB1*0401, and DRB1*0701) published by Southwood et al. (Southwood et al. (1998) *J. Immunol.* 160: 3363). The algorithm calculates the average relative binding (ARB) value for each possible 9-mer core peptide sequence for the entire EBNA2 protein. The higher the ARB value of a peptide, the higher the probability that the peptide would bind to the corresponding HLA-DR allele. Selected peptides that displayed high ARB values were synthesized and purified as described (Kobayashi et al. (2000) *Cancer Res.* 60:5228). The purity (>95%) and identity of peptides were determined by HPLC and mass spectrometry.

In vitro induction of antigen-specific T cell lines using synthetic peptides: The methods used for generating tumor antigen-reactive HTL lines and clones using peptide-stimulated peripheral blood mononuclear cells (PBMC) have been described in detail (Kobayashi et al., supra; and Kobayashi et al. (2001) *Cancer Res.* 61:4773). All blood donors used in the present study were seropositive for EBV. For donors M14 and M44, peptide-pulsed DC were used to stimulate purified $CD4^+$ T cells. Briefly, DC were generated in tissue culture from adherent monocytes that were cultured for 7 days in the presence of GM-CSF and IL-4. A total of $1 \times 10^4$ peptide-pulsed DC (3 μg/ml for 2 hours at room temperature) were irradiated (4,200 rad) and co-cultured with $3 \times 10^4$ autologous purified $CD4^+$ T cells (purified using antibody-coated magnetic beads from Miltenyi Biotech (Auburn, Calif.)) and the $EBNA2_{280-290}$ peptide (3 μg/ml) in each well of a 96-round bottom well culture plate. For the remainder of the blood donors (M1, M2, M9, M15, M20, M24, M25, M69 and M83), total unfractionated PBMC were stimulated with 3 μg/ml peptide in 48-well plates at $5 \times 10^5$ cells/well. Seven days later, all the cultures were re-stimulated individually with peptide (3 μg/ml) and autologous irradiated PBMC. Two days later, human rIL-2 was added to each culture well at a final concentration of 10 IU/ml. After two rounds of re-stimulation, the microcultures were tested for their proliferative responses to peptide as described below. Wells showing a proliferative response to peptide of at least 2.5 fold over background were expanded in 24 or 48-well plates by weekly re-stimulation with peptides and irradiated autologous PBMC. Flow cytometric analysis after 3-rounds of peptide stimulation revealed that >95% of the cells in the cultures were $CD4^+/CD8^-$. Culture medium for all procedures consisted of RPMI-1640 supplemented with 5% human male AB serum, 0.1 mM MEM nonessential amino acids, 1 mM sodium pyruvate, 2 mM L-glutamine, and 50 μg/ml gentamicin.

Analysis of antigen-specific response of T cells: T cells ($3 \times 10^4$/well) were mixed with irradiated APC in the presence of various concentrations of antigen (peptide) in 96-well culture plates. APC consisted of either PBMC ($1 \times 10^5$/well), HLA-DR-expressing L-cells ($3 \times 10^4$/well), or EBV-LCL ($3 \times 10^4$/well). Cells were incubated at 37° C. in a 5% $CO_2$ incubator for 72 hours. During the last 16 hours, each well was pulsed with 0.5 μCi/well of [$^3$H]-thymidine (Amersham Pharmacia Biotech, Piscataway, N.J.). In some cases, culture supernatants were collected for determination of IFN-γ production before the addition of [$^3$H]-thymidine. An ELISA kit (Pharmingen, San Diego, Calif.) was used to measure IFN-γ production. The radioactivity incorporated into DNA, which correlated with cell proliferation, was measured in a liquid scintillation counter after harvesting the cell cultures onto glass fiber filters. To identify the MHC restriction molecules involved in antigen presentation, inhibition of the antigen-induced proliferative response was determined by the addition of anti-HLA-DR Mab L243 (IgG2a, prepared from hybridoma supernatants obtained from ATCC) or anti-HLA-DQ Mab SPVL3 (IgG2a, Beckman Coulter, Inc., Fullerton, Calif.). L243 and SPVL3 recognize non-polymorphic determinants on DR molecules and DQ molecules, respectively, and thus bind to all DR and DQ molecules, respectively. Both antibodies were used at a final concentration of 10 μg/ml and were present throughout the 72 hour assay. All assessments of proliferative responses were carried out at least in triplicate and results correspond to the means. The stimulation index (SI) was calculated by dividing the mean radioactivity (cpm) in the presence of antigen by the mean radioactivity (cpm) in the absence of antigen but in the presence of APC.

Cell-mediated cytotoxicity assays: Cytotoxic activity of $CD4^+$ T cells was determined in a standard $^{51}$Cr-release assay (Lu and Celis (2000) *Cancer Res.* 60:5223). Targets were prepared by incubating EBV-LCL (or T2 cells as a negative control) with or without 10 μg/ml peptide at 37° C. overnight. Target cells were labeled with 300 μCi $^{51}$Cr-sodium chromate (Amersham Pharmacia) per $5 \times 10^6$ cells for 1.5 hours at 37° C. Effector T cells were mixed with $2 \times 10^4$ labeled target at different effector to target (E:T) ratios in 96-round-bottomed-well plates at a final volume of 0.2 ml. After 6-9 hours of incubation at 37° C., 30 μl of supernatant were collected from each well and the percentage of specific lysis was determined according to the formula: {(cpm of the test sample−cpm of spontaneous release)/(cpm of the maximal release−cpm of spontaneous release)}×100. Maximal release was established from wells containing Triton X-100 rather than effector cells, and spontaneous release was established from wells containing medium rather than effector cells. Results show average specific lysis ±SE of triplicate determinations.

EBV-induced B lymphocyte proliferation assays: Infectious EBV stocks were prepared from culture supernatants of the EBV-producing B95-8 cell line. B95-8 cells were seeded at $2 \times 10^5$ cells/ml in complete RPMI 1640 medium and incubated for 14 days at 37° C. without medium exchange. Supernatants from the B95-8 cell cultures were adjusted to contain 10 g of NaCl and 8% (wt/vol) polyethylene glycol (PEG-8000; Sigma) per liter. The precipitates formed after overnight incubation at 4° C. were collected by centrifugation at 7,500 rpm in a Sorvall centrifuge with a GS3 rotor. The pellets were resuspended in 1 ml of complete medium for every 50 ml of original EBV containing supernatant, and were stored at −80° C. until further use. Assays to evaluate EBV-induced B cell proliferation were performed as recently described (Nikiforow et al. (2001) *J. Virol.* 75:3740). Briefly, T cell depleted PBMC were used as a source of B cells, and were produced by negative selection using anti-CD3 coated magnetic beads (Miltenyi). The T cell-depleted PBMC ($4 \times 10^5$ cells) used as a source of B cells were resuspended in 1 ml complete RPMI 1640 medium and 20 μl of concentrated EBV supernatant were added in the absence and presence of various concentrations of T lymphocytes without addition of cytokines. After 10-15 days in culture, the cultures were harvested and the numbers of viable cells were determined using trypan blue exclusion. The percent of $CD23^+$ B cells in each culture condition was estimated by cytofluorometric analysis using a FITC-label specific monoclonal antibody specific for CD23 (Pharmingen).

Example 2

Identification of Potential MHC Promiscuous CD4+ T Cell Epitopes for EBV

Promiscuous MHC class II CD4+ T cell epitopes were identified that could be used to prevent/treat EBV-induced PTLD, a serious complication in solid organ transplant patients. The EBNA2 latent viral antigen was selected as a potential target for inducing T cell responses against PTLD. The amino acid sequence of EBNA2 viral protein was examined for the presence of peptide fragments containing binding motifs for HLA-DR*0101, DR*0401, and DR*0701 using the algorithm tables described by Southwood et al. (supra). Using the cut-off values of ARB necessary to predict 75% of the HLA-DR binders, 35 out of a possible 479 total peptides of a 9-amino acid length (EBNA2 has 487 residues) were predicted as potential binders for HLA-DR1, 23 peptides for -DR4 and only 6 peptides for -DR7. Only 4 peptide sequences from EBNA2 exhibited ARB scores above the cut-off values for all three alleles (Table 1). Peptide EBNA2$_{280-290}$ (Thr-Val-Phe-Tyr-Asn-Ile-Pro-Pro-Met-Pro-Leu; SEQ ID NO:1) was selected as the prime candidate to be evaluated as a highly promiscuous epitope for inducing CD4+ T cell responses in the context of several additional HLA-class II molecules.

TABLE 1

EBNA2 peptides predicted to be promiscuous CD4+ T cell epitopes

| | | | Predicted ARB[1] | | |
|---|---|---|---|---|---|
| EBNA2 position | Sequence (9-mer core) | SEQ ID NO | DR1 (>1.57)[2] | DR4 (>2.617) | DR7 (>9.106) |
| 23-31 | LGNPSLSV | 2 | 3.65 | 4.93 | 34.92 |
| 135-143 | WMANYIVR | 3 | 13.17 | 3.75 | 12.88 |
| 281-289 | VFYNIPPM | 4 | 4.97 | 285.92 | 26.99 |
| 282-290 | FYNIPPMP | 5 | 19.02 | 171.01 | 9.28 |

[1] A greater ARB indicates a greater probability that a peptide will bind to the corresponding MHC allele.
[2] Numbers in parentheses represent the cutoff ARB values suggested by Southwood et al. (supra) to include 75% of peptides binding to the specific allele.

Example 3

Induction of T Cell Responses to Peptide EBNA2$_{280-290}$

The EBNA2$_{280-290}$ peptide was tested for its capacity to stimulate CD4+ T cells isolated from eleven healthy, EBV-seropositive individuals. T cell lines were prepared as described in Example 1 using two different methods. For blood donors M14 and M44, purified CD4+ T cells were stimulated with peptide-pulsed DC and for the remaining nine donors, peptide was added to total unfractionated PBMC. All T cell cultures were re-stimulated 3-4 times weekly with autologous irradiated PBMC and peptide, after which proliferative T cell responses to peptide were evaluated by measuring incorporation of [$^3$H]-thymidine. T cells from a majority of the individuals (7 of 11) were able to respond in vitro to peptide EBNA2$_{280-290}$ in an antigen-specific manner (FIG. 1). The four T cell lines that failed to exhibit peptide-induced proliferative responses either had high background (high proliferation in the absence of peptide) or failed to proliferate.

Example 4

HLA Restriction Analysis of EBNA2$_{280-290}$-Reactive T Cells

To define the HLA restriction alleles of the EBNA2$_{280-290}$ peptide-reactive T cell lines, cell proliferation assays were performed using a panel of HLA-DR-transfected mouse fibroblasts (L cells), with semi-allogeneic human cells used as APC. In addition, anti-HLA-DR or anti-HLA-DQ monoclonal antibodies were tested for their capacity to inhibit the peptide-induced proliferation in response to autologous APC. As depicted in FIG. 2, these experiments showed that peptide EBNA2$_{280-290}$ could be presented to T cells in the context of HLA-DR1 (donor M1), HLA-DQ2 (M14), HLA-DR16 (M24), HLA-DR52 (M44 and M69) and HLA-DR7 (M83). Cytofluorometric analysis revealed that the T cell lines expressed the CD4 marker and did not express CD8, indicating that these cells behaved as typical MHC class II restricted T lymphocytes. The T cell line from donor M9, which previously had responded to peptide EBNA2$_{280-290}$ could not be analyzed for MHC restriction because it was not stable and it ceased to grow in tissue culture.

Example 5

Figure 3:
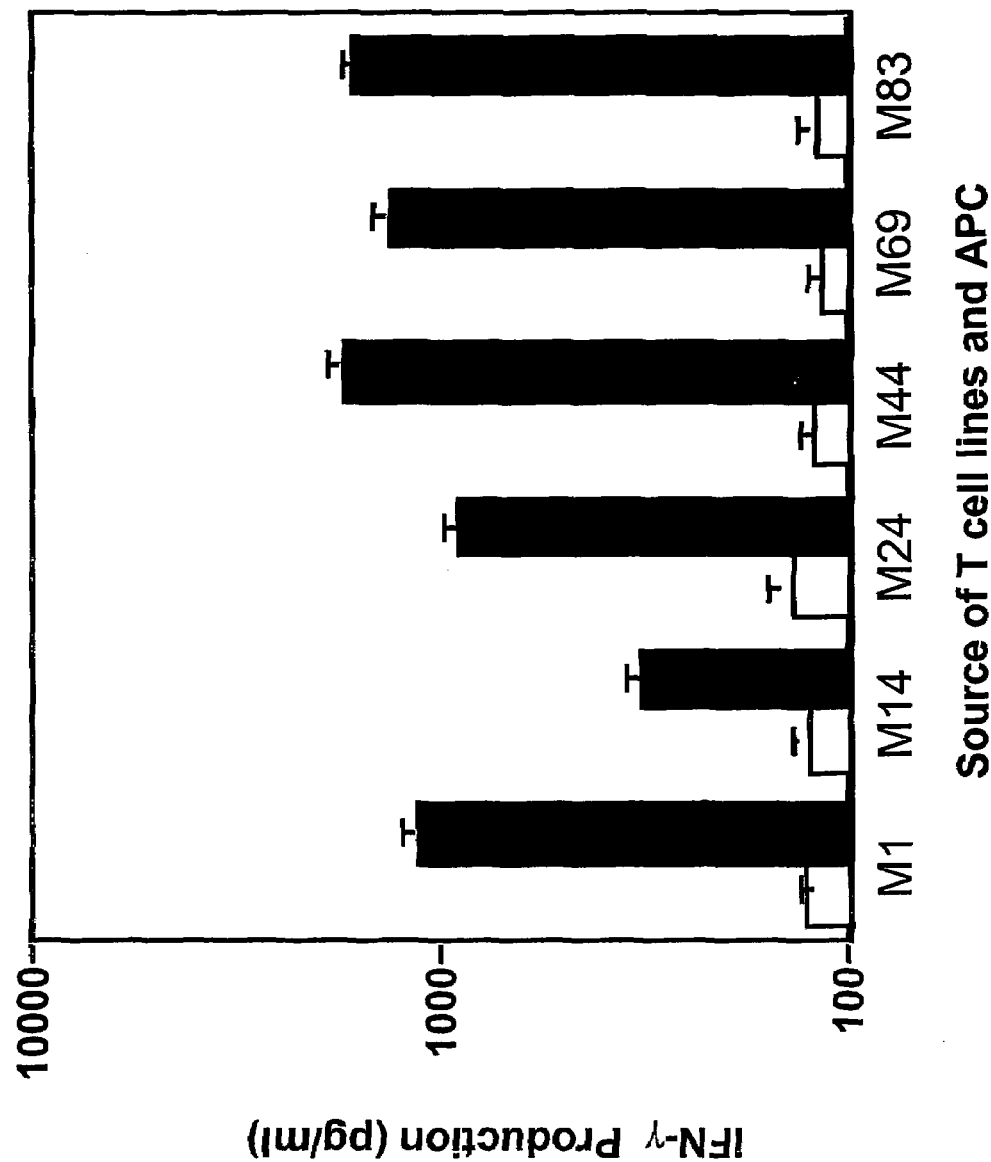
FIG. 3 is a bar graph showing the levels of interferon-γ (IFN-γ) produced by cells of various T cell lines cultured with naturally processed antigen produced by autologous EBV-transformed LCL. IFN-γ production (in pg/ml) by CD4$^+$ T cells was also measured using either the autologous LCL (black bars) or control MHC class II non-expressing T2 LCL (white bars). Identifiers of donors used to produce the T cell lines and autologous LCL are shown on the x-axis. Values shown represent the means of triplicate determinations; error bars, SD.

Recognition of Autologous EBV-Transformed Lymphoblastoid Cells by Peptide-Reactive CD4+ T Cells One of the most critical attributes that peptide-induced anti-EBV CD4+ T cells must exhibit is their capacity to recognize the naturally processed viral antigen expressed by EBV-infected or transformed B lymphocytes. To determine whether EBV transformed lymphoblastoid cell lines (EBV-LCL) that naturally process EBNA2 would be capable of stimulating the peptide-reactive T cell lines, EBV-LCL were generated from all blood donors for use as APC for each corresponding T cell line. IFN-γ secretion by the T cell lines in response to the EBV-LCL was measured. T2 EBV LCL cells, which lack MHC class II molecules, were used as a negative control. These experiments demonstrated that all of the peptide-reactive T cell lines were effective in recognizing antigen presented directly by their corresponding EBV-LCL (FIG. 3). In contrast, no apparent reactivity was observed towards the T2 cells. Thus, the T cell epitope represented by peptide EBNA2$_{280-290}$ can be processed from the EBNA2 protein and expressed on the MHC class II molecules of transformed EBV-LCL, enabling peptide-reactive CD4+ T cells to recognize them efficiently.

Example 6

Figure 4A:
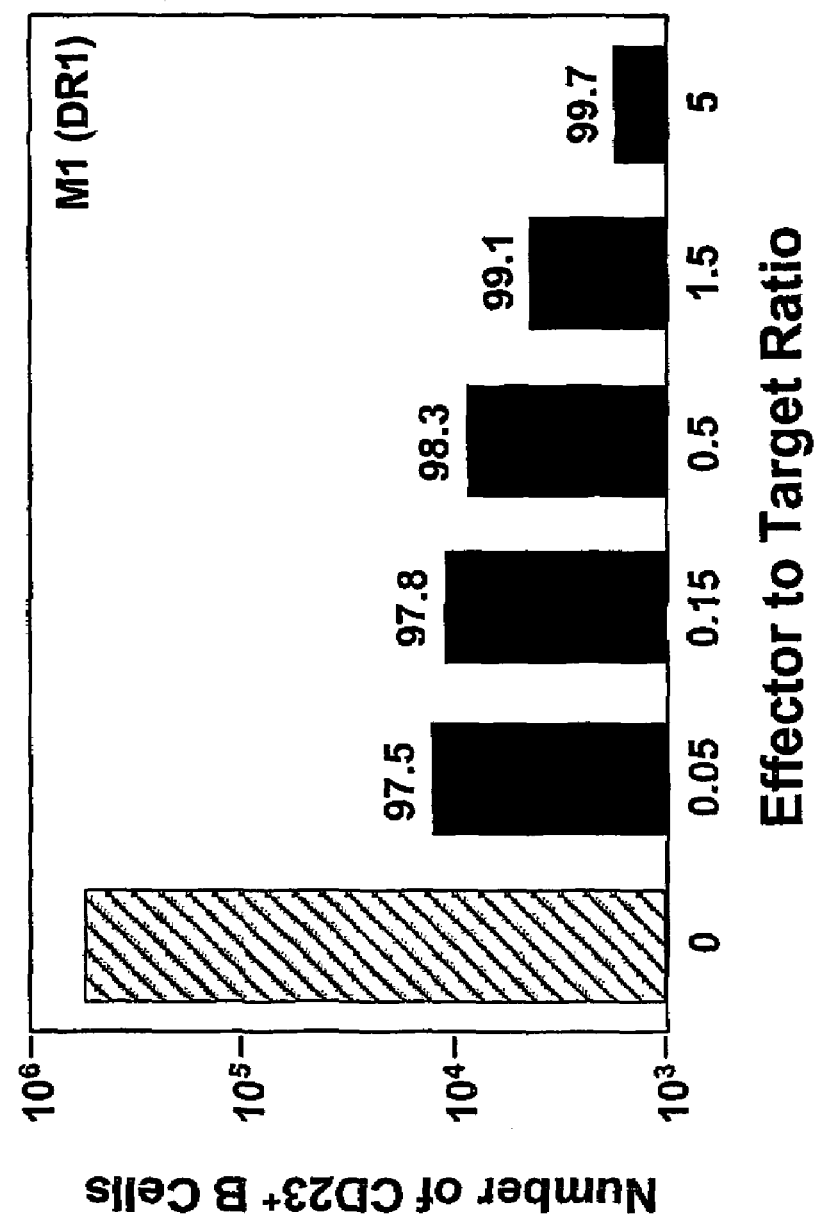
FIGS. 4A-C are a series of bar graphs showing inhibition of EBV-induced B-cell proliferation by $EBNA2_{280-290}$-specific T cells. Three T cell lines (M1 from a DR1-expressing donor (FIG. 4A), M14 from a DQ2-expressing donor (FIG. 4B), and M24 from a DR16-expressing donor (FIG. 4C)) whose responses to $EBNA2_{280-290}$ are restricted by different human MHC class II molecules were evaluated for their ability to inhibit B cell proliferation induced by EBV. Hatched bars represent the numbers of CD23$^+$ B cells obtained in cultures containing EBV but no T cells. Black bars represent the numbers of B cells obtained in cultures in the presence of various numbers (as indicated by the "Effector to Target Ratio" on the x-axes) of $EBNA2_{280-290}$-specific T cells. White bars (only in FIG. 4B showing data from the T cell line derived from donor M14) indicate values obtained in the presence of a control irrelevant T cell line specific for the MAGE3 antigen. Numbers above black and white bars denote the percent inhibition of the number of CD23$^+$ B cells in each culture (compared to data obtained in control cultures without T cells).
Figure 4B:
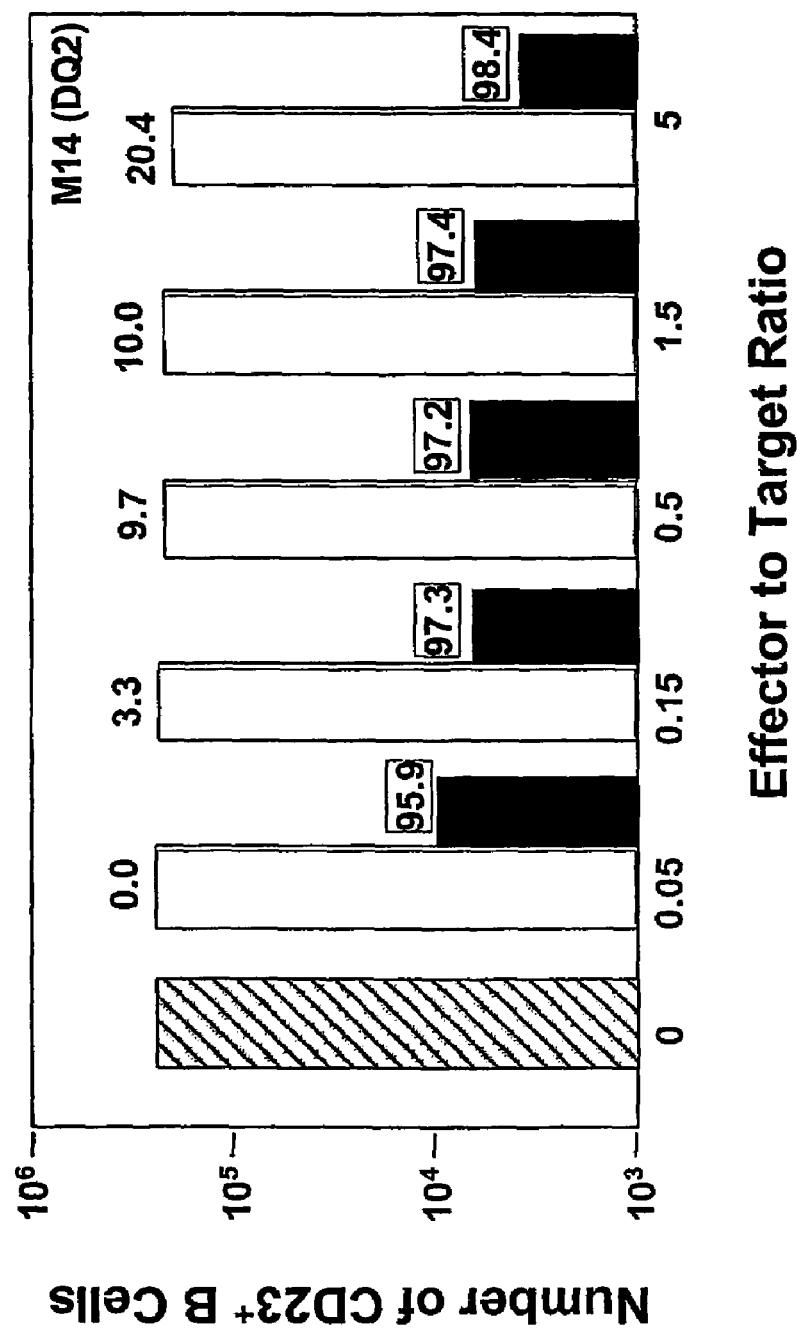
Figure 4C:
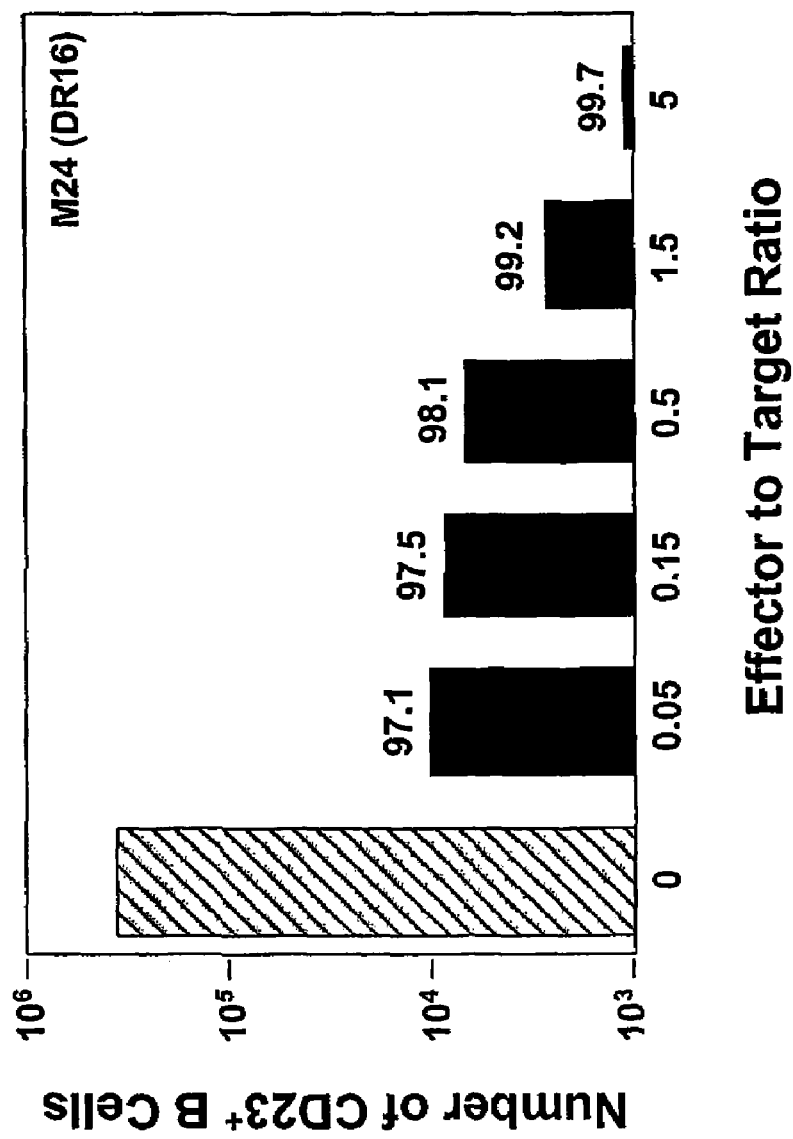

Inhibition of EBV-Induced B-Cell Proliferation by EBNA2$_{280-290}$-Reactive CD4+ T Cells CD4+ "helper" T cells are capable of exhibiting effector activity either in the form of cytotoxicity or via the production of lymphokines against viral infections. Moreover, CD4+ T cells also are capable of suppressing the early stages of B-cell proliferation and transformation by EBV (Nikiforow et al., supra), whereas CD8+ T cells appear to play a more significant role in controlling EBV in the latent infection state (Rickinson and Moss, supra). Thus, antiviral activity of EBNA2$_{280-290}$-reactive CD4+ T cells was examined to determine whether such cells would be capable of controlling the early events of EBV-induced B-cell proliferation that ultimately lead to malignant transformation. Various numbers of EBNA2$_{280-290}$-reactive CD4$^+$ T cells derived from three separate donors (M1, M14 and M24) were evaluated for their ability to inhibit EBV-mediated B-cell proliferation in a 10 to 15-day culture assay. For donor M14, a T cell clone specific for an irrelevant non-EBV antigen (MAGE3) was included as a negative control. In all cases the EBV-reactive T cells were highly effective at inhibiting the proliferation of CD23$^+$ B lymphocytes induced by EBV infection (FIG. 4). In contrast, the MAGE3-reactive T cell clone did not have a significant effect in the proliferation of the B cells, indicating that the inhibitory effect of the EBV-reactive T cells was antigen-specific.

Figure 5A:
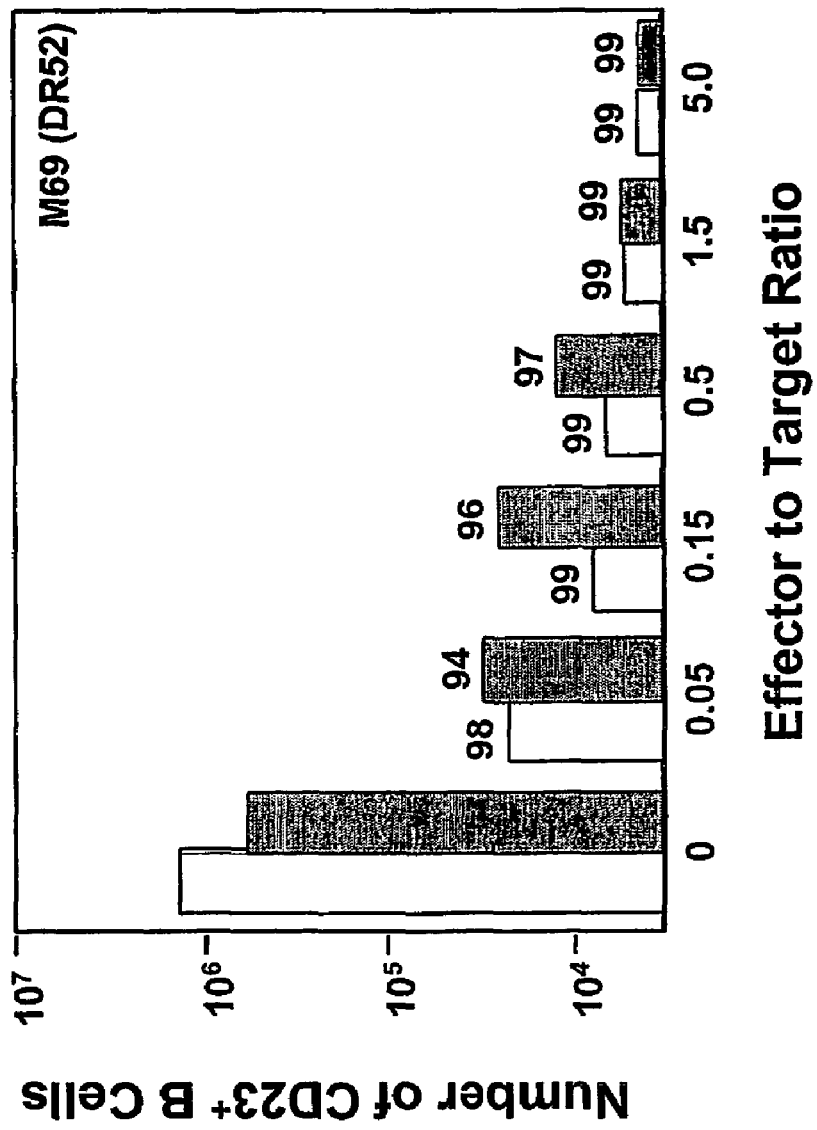
FIGS. 5A, 5B, and 5C are bar graphs showing the effect of Cyclosporin A (CsA) on the effector function of $EBNA2_{280-290}$-specific T cells. In the experiment shown in FIG. 5A, various numbers of cells of the CD4$^+$ T cell line from DR52-expressing donor M69 (as indicated by the "Effector to Target Ratio" on the x-axis) were tested for their capacity to inhibit the EBV-mediated expansion of CD23$^+$ B cells in the presence (shaded bars) or absence (white bars) of 1 μg/ml CsA. Numbers above each bar represent the percent inhibition of B-cell expansion in response to various numbers of T cells compared to the number of B cells obtained from a control culture containing no T cells.
Figure 5B:
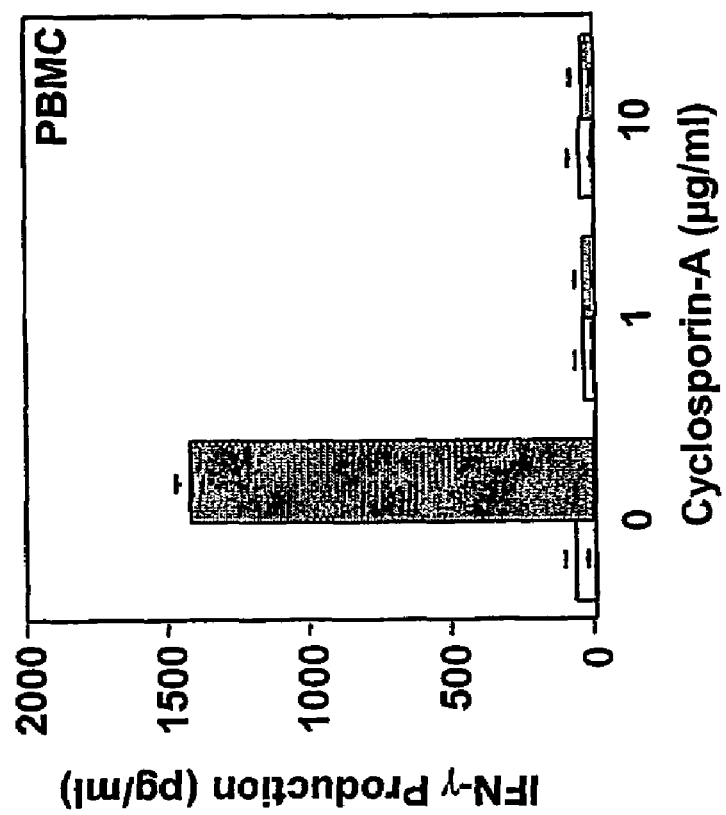
Figure 5C:
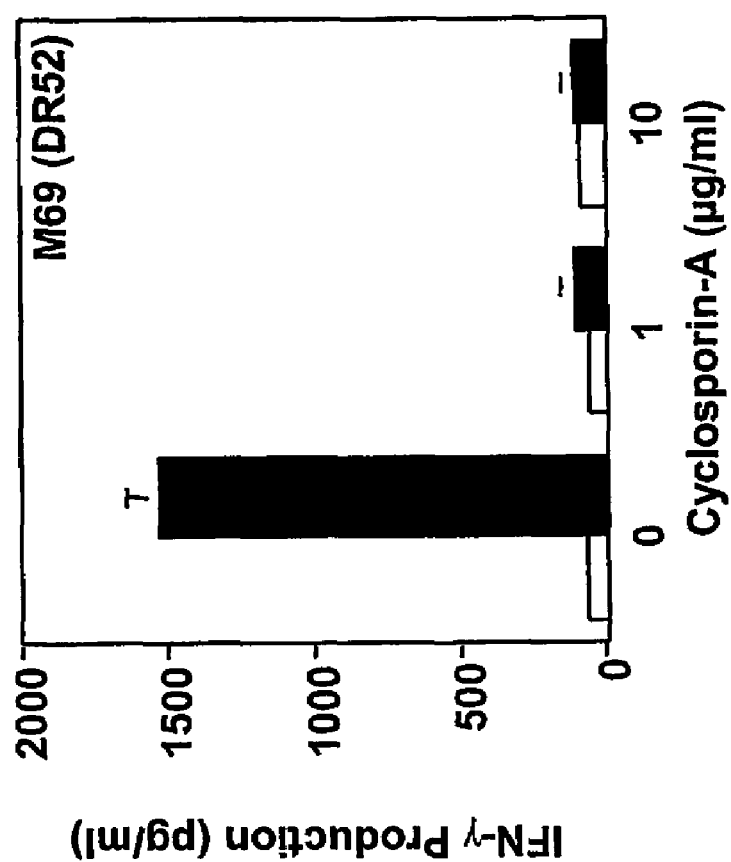
Figure 6:
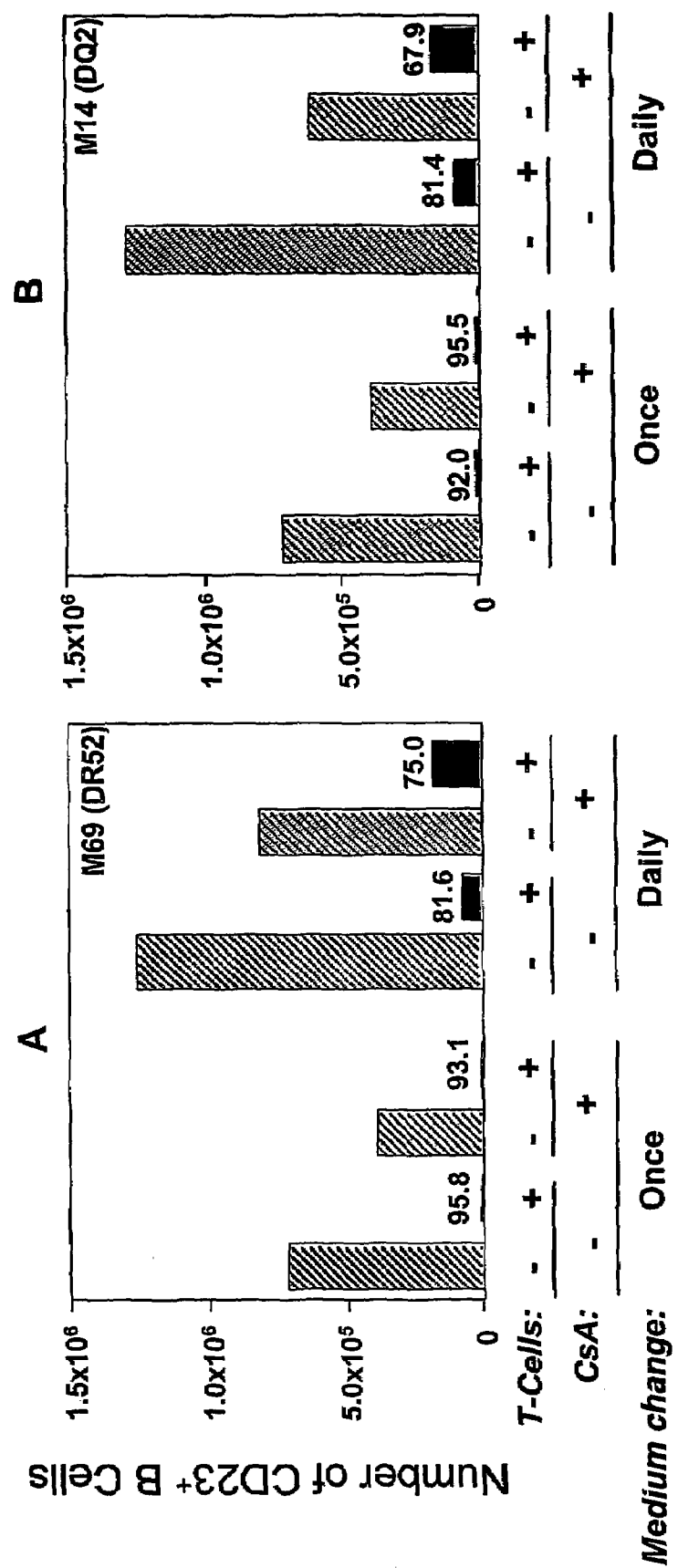
FIGS. 6A and B are a pair of bar graphs showing inhibition of EBV-induced B cell proliferation by $EBNA2_{280-290}$-specific T cells of T cell lines from DR52-expressing donor M69 (FIG. 6A) and DQ2-expressing donor M14 (FIG. 6B) in the continuous presence of CsA. CsA was either added only once (day 0) or was added on a daily basis, as indicated by "Medium Changed." Hatched bars: cultures without T cells; black bars: cultures with T cells at an effector to target ratio of 3:1. Numbers above each black bar represent the percent inhibition of B-cell expansion induced by T cells compared to the cultures carried out under the same conditions, but in the absence of T cells. Values represent the means of triplicate determinations.

These results suggested that MHC class II-restricted CD4$^+$ T cells specific for the EBNA2$_{280-290}$ epitope would be able to prevent or control PTLD in solid organ transplant patients. However, these patients usually receive immunosuppressive therapy with drugs such as Cyclosporin-A (CsA) to prevent the rejection of the transplanted organs. CsA and other immunosuppressive agents can inhibit some of the TCR-mediated effector functions of T lymphocytes, such as the production of lymphokines (Sigal and Dumont (1992) *Annu. Rev. Immunol.* 10:519). Consequently, the ability of CsA to diminish the anti-viral effect of EBNA2$_{280-290}$-specific T cells from donor M69 (DR52-restricted) was evaluated. As shown in FIG. 5A, the EBNA2$_{280-290}$-specific T cells were very effective in inhibiting the EBV-induced proliferation of B-lymphocytes even in the presence of CsA (at 1 µg/ml) added at the initiation of the experiments. On the other hand, the same concentration of CsA was capable of suppressing the production of IFN-γ by PBMC from donor M69 stimulated with anti-CD3 antibodies (FIG. 5B), indicating that this compound was active at the dose studied. Similarly, CsA also inhibited the production of INF-γ by EBNA2$_{280-290}$-specific T cells induced by antigen presented by EBV-LCL (FIG. 5C). In another set of experiments performed under more strenuous conditions, CsA was added to some of the cultures every day (to a final 1 µg/ml) to take into account possible effects due to the decrease of the drug's potency during the 10-day experiment. Under these conditions, the EBNA2$_{280-290}$-specific T cells from donors M69 (DR52-restricted) and M14 (DQ2-restricted) still were capable of significantly inhibiting the EBV-induced B cell proliferation by more than 70% (FIG. 6). Overall, these results suggested that even in the presence of high doses of CsA, EBNA2$_{280-290}$-specific CD4$^+$ T cells may be effective in preventing B lymphocyte proliferation induced by EBV.

Example 7

Cytolytic Activity of EBNA2$_{280-290}$-Specific CD4$^+$ T Cells

Figure 7:
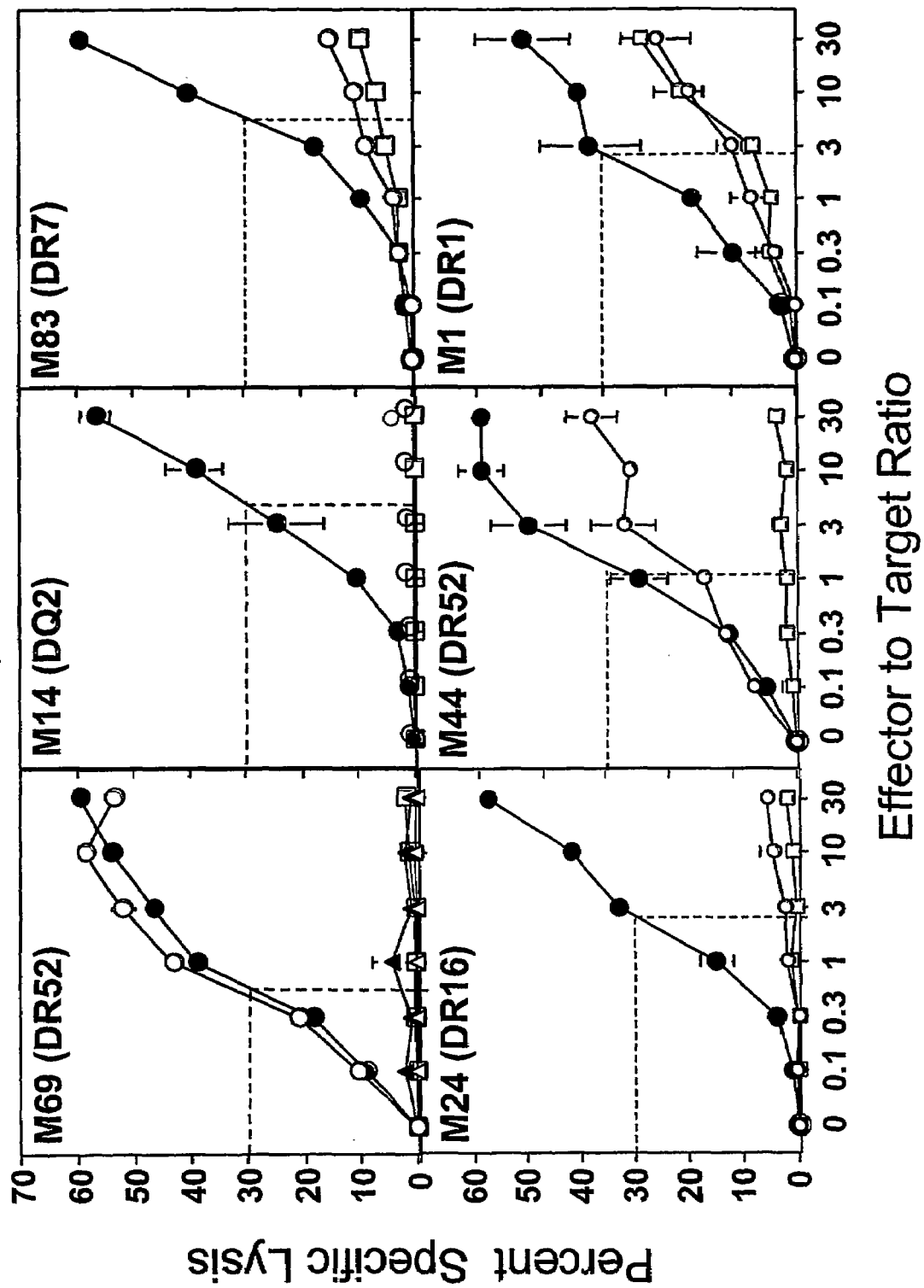
FIG. 7 is a series of graphs showing cytolytic activity (expressed as "Percent Specific Lysis") of cells of EBNA2$_{280-290}$-specific T cell lines derived from the indicated donors. The T cells were tested at various E:T ratios for their capacity to kill several target cells: autologous EBV-LCL (white circles); EBNA2$_{280-290}$ peptide-pulsed autologous EBV-LCL (black circles); control MHC class II non-expressing T2 cells (white squares). Additional negative control target cells for donor M69 (top left panel) were: allogeneic EBV-LCL from donor M35 (DR4/15, DR51/53, DQ6/7) without exogenous peptide (white triangles) and pulsed with peptide (black triangles).

The results presented in Example 6 suggested that a CsA-insensitive effector mechanism such as cell-mediated cytotoxicity could be used by EBNA2$_{280-290}$-reactive CD4$^+$ T cells to inhibit EBV infection and subsequent B-cell proliferation. The cytotoxic activity of the six EBNA2$_{280-290}$-specific T cell lines was evaluated against various target cells. As shown in FIG. 7, the CD4$^+$ T cell lines from all six donors were capable of killing peptide-pulsed autologous target cells. In all cases, with the exception of donor M1, no cytotoxicity was detected against the MHC class II-negative T2 cells, indicating the requirement of TCR interaction with peptide MHC complexes on the target cells. Moreover, in the case of donors M69 and M44 (HLA-DR52-restricted), the T cells also were effective in killing the autologous EBV-transformed LCL in the absence of exogenously added peptide, indicating that the amount of naturally processed EBNA2$_{280-290}$ epitope in these cells was sufficient to allow the cytolytic reaction to take place. Furthermore, the EBNA2$_{280-290}$-reactive T cell line from donor M69 was not able to kill an EBV-LCL from an HLA-DR52 negative donor, regardless of whether the cells were pulsed with synthetic peptide or not (FIG. 7, top left panel). These data indicate that lysis by these cells is MHC-restricted and requires the presence of the specific MHC peptide complexes on the target cells. It was noted that the potency of the cytotoxic function of the M69 and M44 T cell lines was different when compared to the other cell lines. While 30% specific lysis (50% of the maximal activity) was obtained at an effector to target ratio of 1:1 or less in the M69 and M44 T cell lines, an approximately 3-fold greater E:T ratio was required to obtain the same level of cytotoxicity with the other T cell lines (FIG. 7, dashed lines). Thus, the M69 and M44 T cell lines were significantly more potent in killing their target cells than the other T cell lines, which could explain the inability of the latter lines to kill the EBV-LCL in the absence of exogenously added peptide.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for eliciting an immune response against EBV in a subject, said method comprising:
   (a) providing a subject identified as being in need of vaccination against EBV and as expressing one or more HLA class II molecules selected from the group consisting of HLA-DR1, HLA-DR7, HLA-DR16, HLA-DR52, HLA-DQ2, and HLA-DQ7; and
   (b) administering to said subject an EBV peptide epitope having the amino acid sequence set forth in SEQ ID NO:1.

2. The method of claim 1, further comprising administering to said subject one or more immune-enhancing agents.

3. The method of claim 2, wherein said one or more immune-enhancing agents comprise an adjuvant.

4. The method of claim 3, wherein said adjuvant is a mineral oil-in-water emulsion adjuvant.

5. The method of claim 2, wherein said one or more immune-enhancing agents comprise a cytokine.

6. The method of claim 5, wherein said cytokine is granulocyte macrophage-colony stimulating factor.

7. The method of claim 2, wherein said one or more immune-enhancing agents comprise a co-stimulatory molecule.

8. The method of claim 1, wherein said subject has, is suspected of having, or is at risk for a post-transplant lymphoproliferative disorder.

* * * * *

SEQUENCE LISTING

<160> NUMBER OF SEQ ID NOS: 6

<210> SEQ ID NO 1
<211> LENGTH: 11
<212> TYPE: PRT
<213> ORGANISM: Epstein-Barr virus

<400> SEQUENCE: 1

Thr Val Phe Tyr Asn Ile Pro Pro Met Pro Leu

-continued

```
<210> SEQ ID NO 2
<211> LENGTH: 8
<212> TYPE: PRT
<213> ORGANISM: Epstein-Barr virus

<400> SEQUENCE: 2

Leu Gly Asn Pro Ser Leu Ser Val
1               5

<210> SEQ ID NO 3
<211> LENGTH: 8
<212> TYPE: PRT
<213> ORGANISM: Epstein-Barr virus

<400> SEQUENCE: 3

Trp Met Ala Asn Tyr Ile Val Arg
1               5

<210> SEQ ID NO 4
<211> LENGTH: 8
<212> TYPE: PRT
<213> ORGANISM: Epstein-Barr virus

<400> SEQUENCE: 4

Val Phe Tyr Asn Ile Pro Pro Met
1               5

<210> SEQ ID NO 5
<211> LENGTH: 8
<212> TYPE: PRT
<213> ORGANISM: Epstein-Barr virus

<400> SEQUENCE: 5

Phe Tyr Asn Ile Pro Pro Met Pro
1               5

<210> SEQ ID NO 6
<211> LENGTH: 9
<212> TYPE: PRT
<213> ORGANISM: Epstein-Barr virus

<400> SEQUENCE: 6

Phe Tyr Asn Ile Pro Pro Met Pro Leu
1               5
```